US011779320B2

(12) United States Patent
Walters et al.

(10) Patent No.: US 11,779,320 B2
(45) Date of Patent: *Oct. 10, 2023

(54) VASCULAR CLOSURE DEVICE

(71) Applicant: Teleflex Life Sciences Limited, Valletta (MT)

(72) Inventors: Greg Walters, Exton, PA (US); Joseph T. Grintz, Glenmoore, PA (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,455

(22) Filed: May 16, 2022

(65) Prior Publication Data

US 2022/0273277 A1 Sep. 1, 2022

Related U.S. Application Data

(60) Continuation of application No. 16/568,588, filed on Sep. 12, 2019, now Pat. No. 11,364,024, which is a
(Continued)

(51) Int. Cl.
*A61B 17/00* (2006.01)
*A61B 17/04* (2006.01)

(52) U.S. Cl.
CPC ...... *A61B 17/0057* (2013.01); *A61B 17/0469* (2013.01); *A61B 2017/00623* (2013.01);
(Continued)

(58) Field of Classification Search
CPC ............ A61B 17/0057; A61B 17/0469; A61B 2017/0496; A61B 2017/00575;
(Continued)

(56) References Cited

U.S. PATENT DOCUMENTS 3,125,095 A 3/1964 Kaufman et al.
4,665,918 A 5/1987 Garza et al.
(Continued)

FOREIGN PATENT DOCUMENTS

EP 0474752 B1 6/1995
EP 0766947 A2 4/1997
(Continued)

OTHER PUBLICATIONS

International Search Report and the Written Opinion from International Patent Application PCT/US2017/013314, dated Apr. 18, 2017, 11 pp.

(Continued)

*Primary Examiner* — Majid Jamialahmadi
(74) *Attorney, Agent, or Firm* — Gregory A. Grissett; Joseph P. Mathew

(57) ABSTRACT

A vascular closure device includes a release component, a delivery component, a sealing device and at least one actuator. The release component is elongate along a longitudinal direction, and defines a distal end and a proximal end. The delivery component extends along the release component such that at least the release component is movable relative to the delivery component. The delivery component includes a delivery tube body and defines a delivery tube channel. The sealing device has a toggle that is at least partially disposed within the release tube, a suture that is attached to the toggle and extends through the delivery tube channel, and a plug that is attached to the suture proximal to the toggle. The actuator is coupled to the release component and is in communication with the suture such that actuation of the actuator causes (i) the release component to move the proximal direction relative to the delivery component so as to release the toggle from the release component, and (ii) the suture to be pulled in a
(Continued)

proximal direction to thereby place the filament in tension and urge the toggle against a distal end of the delivery component such that the toggle is oriented in a sealing position.

18 Claims, 15 Drawing Sheets

Related U.S. Application Data division of application No. 15/105,180, filed as application No. PCT/US2014/068694 on Dec. 5, 2014, now Pat. No. 10,448,937.

(60) Provisional application No. 61/920,207, filed on Dec. 23, 2013.

(52) U.S. Cl.
CPC ............... *A61B 2017/00654* (2013.01); *A61B 2017/00659* (2013.01); *A61B 2017/0496* (2013.01)

(58) Field of Classification Search
CPC A61B 2017/00637; A61B 2017/00641; A61B 2017/00646; A61B 2017/00659; A61B 2017/00654; A61B 2017/00676; A61B 2017/00672
See application file for complete search history.

(56) References Cited

U.S. PATENT DOCUMENTS

| | | |
|---|---|---|
| 4,760,847 A | 8/1988 | Vaillancourt |
| 4,798,594 A | 1/1989 | Hillstead |
| 4,890,612 A | 1/1990 | Kensey |
| 4,895,346 A | 1/1990 | Steigerwald |
| 4,895,565 A | 1/1990 | Hillstead |
| 4,990,151 A | 2/1991 | Wallsten |
| 5,021,059 A * | 6/1991 | Kensey ............... A61B 17/0057 606/232 |
| 5,026,377 A | 6/1991 | Burton et al. |
| 5,041,095 A | 8/1991 | Littrell |
| 5,059,183 A | 10/1991 | Semrad |
| 5,222,974 A | 6/1993 | Kensey et al. |
| 5,282,827 A | 2/1994 | Kensey et al. |
| 5,292,309 A | 3/1994 | Tassel et al. |
| 5,306,254 A | 4/1994 | Nash et al. |
| 5,322,508 A | 6/1994 | Viera |
| 5,324,306 A | 6/1994 | Makower et al. |
| 5,360,414 A | 11/1994 | Yarger |
| 5,363,847 A | 11/1994 | Viera |
| 5,411,520 A | 5/1995 | Nash et al. |
| 5,531,759 A | 7/1996 | Kensey et al. |
| 5,545,178 A | 8/1996 | Kensey et al. |
| 5,643,318 A | 7/1997 | Tsukernik et al. |
| 5,662,681 A | 9/1997 | Nash et al. |
| 5,700,277 A | 12/1997 | Nash et al. |
| 5,702,421 A | 12/1997 | Schneidt |
| 5,843,124 A | 12/1998 | Hammerslag |
| 6,010,520 A | 1/2000 | Pattison |
| 6,056,768 A | 5/2000 | Cates et al. |
| 6,090,130 A | 7/2000 | Nash et al. |
| 6,107,004 A | 8/2000 | Donadio, III |
| 6,179,863 B1 | 1/2001 | Kensey et al. |
| 6,245,054 B1 | 6/2001 | Fuimaono et al. |
| 6,425,911 B1 | 7/2002 | Akerfeldt et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,494,848 B1 | 12/2002 | Sommercorn et al. |
| 6,682,489 B2 | 1/2004 | Tenerz et al. |
| 6,860,895 B1 | 3/2005 | Akerfeldt et al. |
| 7,037,322 B1 | 5/2006 | Sing et al. |
| 7,044,916 B2 | 5/2006 | Tenerz et al. |
| 7,073,509 B2 | 7/2006 | Tenerz et al. |
| 7,094,209 B2 | 8/2006 | Egnelöv et al. |
| 7,285,097 B2 | 10/2007 | Tenerz et al. |
| 7,316,704 B2 | 1/2008 | Bagaoisan et al. |
| 7,597,705 B2 | 10/2009 | Forsberg et al. |
| 7,618,436 B2 | 11/2009 | Forsberg |
| 7,648,493 B2 | 1/2010 | Forsberg et al. |
| 7,695,493 B2 | 4/2010 | Saadat et al. |
| 7,850,654 B2 | 12/2010 | Belhe et al. |
| 7,905,902 B2 | 3/2011 | Huitema et al. |
| 8,029,533 B2 | 10/2011 | Bagaoisan et al. |
| 8,097,007 B2 | 1/2012 | Evans et al. |
| 8,137,321 B2 | 3/2012 | Argentine |
| 8,273,094 B2 | 9/2012 | Belhe et al. |
| 8,337,522 B2 | 12/2012 | Ditter |
| 8,382,793 B2 | 2/2013 | Egnelöv et al. |
| 8,435,256 B2 | 5/2013 | Lehe et al. |
| 8,444,673 B2 | 5/2013 | Thielen et al. |
| 8,540,750 B2 | 9/2013 | Tegels |
| 8,685,059 B2 | 4/2014 | Walters |
| 8,870,917 B2 | 10/2014 | Walters |
| 8,974,476 B2 | 3/2015 | Tegels |
| 9,089,363 B2 | 7/2015 | Dooney et al. |
| 9,675,371 B2 | 6/2017 | Shimon |
| 9,757,104 B2 | 9/2017 | Walters et al. |
| 10,154,835 B2 | 12/2018 | Walters et al. |
| 10,383,611 B2 | 8/2019 | Walters et al. |
| 10,390,810 B2 | 8/2019 | Walters et al. |
| 10,448,937 B2 | 10/2019 | Walters et al. |
| 10,485,524 B2 | 11/2019 | Walters et al. |
| 10,555,727 B2 | 2/2020 | Walters et al. |
| 10,639,019 B2 | 5/2020 | Walters |
| 10,668,253 B2 | 6/2020 | Jacobs |
| 10,682,128 B2 | 6/2020 | Walters et al. |
| 11,020,224 B2 | 6/2021 | Jacobs |
| 11,123,053 B2 | 9/2021 | Walters et al. |
| 11,364,024 B2 | 6/2022 | Walters et al. |
| 11,419,592 B2 | 8/2022 | Walters et al. |
| 11,576,663 B2 | 2/2023 | Walters et al. |
| 11,589,855 B2 | 2/2023 | Walters et al. |
| 2001/0003158 A1 | 6/2001 | Kensey et al. |
| 2001/0044639 A1 | 11/2001 | Levinson |
| 2002/0022822 A1 | 2/2002 | Cragg et al. |
| 2003/0078616 A1 | 4/2003 | Ginn et al. |
| 2004/0138674 A1 | 7/2004 | Egnelov et al. |
| 2004/0147950 A1 | 7/2004 | Mueller et al. |
| 2004/0204741 A1 | 10/2004 | Egnelov et al. |
| 2004/0267308 A1 | 12/2004 | Bagaoisan et al. |
| 2005/0085856 A1 | 4/2005 | Ginn |
| 2005/0107820 A1 | 5/2005 | Forsberg et al. |
| 2005/0107826 A1 | 5/2005 | Zhu et al. |
| 2005/0107827 A1 | 5/2005 | Paprocki |
| 2005/0125030 A1 | 6/2005 | Forsberg et al. |
| 2005/0277961 A1 | 12/2005 | Stone et al. |
| 2006/0058844 A1 | 3/2006 | White et al. |
| 2006/0217664 A1 | 9/2006 | Hattler et al. |
| 2006/0229673 A1 | 10/2006 | Forsberg |
| 2007/0123936 A1 | 5/2007 | Goldin et al. |
| 2007/0282373 A1 | 12/2007 | Ashby et al. |
| 2008/0082123 A1 | 4/2008 | Forsberg et al. |
| 2008/0157017 A1 | 7/2008 | Macatangay et al. |
| 2008/0306509 A1 | 12/2008 | Osborne |
| 2009/0054926 A1 | 2/2009 | Pipenhagen et al. |
| 2009/0088793 A1 | 4/2009 | Bagaoisan et al. |
| 2009/0099598 A1 | 4/2009 | McDevitt et al. |
| 2009/0137870 A1 | 5/2009 | Bakos et al. |
| 2009/0171387 A1 | 7/2009 | Pipenhagen et al. |
| 2009/0248064 A1 | 10/2009 | Preinitz |
| 2009/0312790 A1 | 12/2009 | Forsberg et al. |
| 2009/0318894 A1 | 12/2009 | Lafitte et al. |
| 2010/0016887 A1 | 1/2010 | Inderbitzi |
| 2010/0168789 A1 | 7/2010 | Bagaoisan et al. |
| 2010/0179589 A1 | 7/2010 | Roorda et al. |
| 2010/0185216 A1 | 7/2010 | Garrison et al. |
| 2011/0004162 A1 | 1/2011 | Tal |
| 2011/0046665 A1 | 2/2011 | Green et al. |
| 2011/0054456 A1 | 3/2011 | Thompson et al. |
| 2011/0160765 A1 | 6/2011 | Melmed et al. |

(56) References Cited

U.S. PATENT DOCUMENTS

| | | |
|---|---|---|
| 2011/0208222 A1 | 8/2011 | Ljahnicky et al. |
| 2011/0213414 A1 | 9/2011 | McGuckin, Jr. et al. |
| 2011/0213415 A1 | 9/2011 | McGuckin, Jr. et al. |
| 2011/0301619 A1 | 12/2011 | Walters |
| 2012/0010634 A1 | 1/2012 | Crabb et al. |
| 2012/0022585 A1 | 1/2012 | Atanasoska et al. |
| 2012/0065668 A1 | 3/2012 | Ginn et al. |
| 2012/0071919 A1 | 3/2012 | Pipenhagen et al. |
| 2012/0083829 A1 | 4/2012 | Ginn et al. |
| 2012/0101525 A1 | 4/2012 | Jenson et al. |
| 2012/0109192 A1 | 5/2012 | Egnelöv et al. |
| 2012/0116446 A1 | 5/2012 | Green et al. |
| 2012/0143244 A1 | 6/2012 | Hill et al. |
| 2012/0143245 A1 | 6/2012 | Tegels |
| 2012/0143249 A1 | 6/2012 | Jenson et al. |
| 2012/0158044 A1 | 6/2012 | Jenson et al. |
| 2012/0165854 A1 | 6/2012 | Pipenhagen et al. |
| 2012/0245517 A1 | 9/2012 | Tegels |
| 2012/0245597 A1 | 9/2012 | Tegels |
| 2012/0245624 A1 | 9/2012 | Glazier et al. |
| 2012/0283770 A1 | 11/2012 | Kramer et al. |
| 2012/0296275 A1 | 11/2012 | Martin et al. |
| 2013/0006297 A1 | 1/2013 | Drasler |
| 2013/0006298 A1 | 1/2013 | Terwey |
| 2013/0025588 A1 | 1/2013 | Bosel |
| 2013/0035719 A1 | 2/2013 | Hill et al. |
| 2013/0072949 A1 | 3/2013 | Halac et al. |
| 2013/0079802 A1 | 3/2013 | Halac et al. |
| 2013/0103077 A1 | 4/2013 | Ditter |
| 2013/0131718 A1 | 5/2013 | Jenson et al. |
| 2013/0144316 A1 | 6/2013 | McCrea et al. |
| 2013/0150884 A1 | 6/2013 | Belhe et al. |
| 2013/0178895 A1 | 7/2013 | Walters et al. |
| 2013/0226227 A1 | 8/2013 | Terwey |
| 2014/0039264 A1 | 2/2014 | Heiman |
| 2014/0046217 A1 | 2/2014 | Lim |
| 2014/0046220 A1 | 2/2014 | Nelson |
| 2014/0094846 A1 | 4/2014 | Lim et al. |
| 2014/0188160 A1 | 7/2014 | Tegels |
| 2014/0200611 A1 | 7/2014 | Walters |
| 2014/0236088 A1 | 8/2014 | Al-Rashdan et al. |
| 2014/0309686 A1 | 10/2014 | Ginn et al. |
| 2014/0364899 A1 | 12/2014 | Ginn et al. |
| 2015/0068009 A1 | 3/2015 | Walters |
| 2015/0100083 A1 | 4/2015 | Walters et al. |
| 2015/0173794 A1 | 6/2015 | Kurth et al. |
| 2016/0228109 A1 | 8/2016 | Jacobs et al. |
| 2017/0135725 A1 | 5/2017 | Tegels |
| 2017/0333015 A1 | 11/2017 | Walters et al. |
| 2019/0015204 A1 | 1/2019 | Jacobs |
| 2019/0015637 A1 | 1/2019 | Jacobs |
| 2019/0110781 A1 | 4/2019 | Walters et al. |
| 2019/0336116 A1 | 11/2019 | Walters et al. |
| 2020/0000448 A1 | 1/2020 | Walters et al. |
| 2020/0146661 A1 | 5/2020 | Walters et al. |
| 2020/0289101 A1 | 9/2020 | Walters |
| 2022/0338852 A1 | 10/2022 | Walters |

FOREIGN PATENT DOCUMENTS

| | | |
|---|---|---|
| EP | 0797953 A2 | 10/1997 |
| EP | 1169968 A1 | 1/2002 |
| EP | 1222896 A2 | 7/2002 |
| EP | 1254634 A1 | 11/2002 |
| EP | 0664687 B2 | 8/2003 |
| EP | 1371333 A1 | 12/2003 |
| EP | 1413255 A1 | 4/2004 |
| EP | 1440661 A1 | 7/2004 |
| EP | 1163020 B1 | 9/2004 |
| EP | 1532929 A1 | 5/2005 |
| EP | 1658811 A1 | 5/2006 |
| EP | 1695667 A1 | 8/2006 |
| EP | 1836967 A1 | 9/2007 |
| EP | 1836968 A1 | 9/2007 |
| EP | 2055236 A1 | 5/2009 |
| EP | 2064999 A2 | 6/2009 |
| EP | 2213247 A1 | 8/2010 |
| EP | 2215974 A2 | 8/2010 |
| EP | 1919367 B1 | 10/2011 |
| EP | 1874195 B1 | 1/2012 |
| EP | 1893100 B1 | 3/2012 |
| EP | 2227148 B1 | 4/2012 |
| EP | 1893099 B1 | 6/2012 |
| EP | 1893098 B1 | 1/2014 |
| EP | 2611366 B1 | 7/2014 |
| EP | 2605707 B1 | 10/2014 |
| EP | 1773438 B1 | 1/2017 |
| WO | 1989011301 A1 | 11/1989 |
| WO | 1990014796 A1 | 12/1990 |
| WO | 1992014396 A1 | 9/1992 |
| WO | 1993008743 A1 | 5/1993 |
| WO | 1993008746 A3 | 8/1993 |
| WO | 1994007421 A1 | 4/1994 |
| WO | 1998005259 A1 | 2/1998 |
| WO | 1999022646 A1 | 5/1999 |
| WO | 2000078226 A1 | 12/2000 |
| WO | 2003094740 A1 | 11/2003 |
| WO | 2004096056 A2 | 11/2004 |
| WO | 2005002451 A1 | 1/2005 |
| WO | 2005039387 A2 | 5/2005 |
| WO | 2005060514 A2 | 7/2005 |
| WO | 2006075228 A1 | 7/2006 |
| WO | 2006110615 A2 | 10/2006 |
| WO | 2007035187 A2 | 3/2007 |
| WO | 2008036634 A1 | 3/2008 |
| WO | 2009005722 A1 | 1/2009 |
| WO | 2009025836 A1 | 2/2009 |
| WO | 2009029914 A1 | 3/2009 |
| WO | 2009035921 A2 | 3/2009 |
| WO | 2009088440 A1 | 7/2009 |
| WO | 2009088441 A1 | 7/2009 |
| WO | 2009112930 A2 | 9/2009 |
| WO | 2010129042 A1 | 11/2010 |
| WO | 2011014244 A1 | 2/2011 |
| WO | 2011019374 A1 | 2/2011 |
| WO | 2011025529 A1 | 3/2011 |
| WO | 2011025543 A2 | 3/2011 |
| WO | 2011037635 A1 | 3/2011 |
| WO | 2011146729 A2 | 11/2011 |
| WO | 2011156498 A1 | 12/2011 |
| WO | 2012009007 A1 | 1/2012 |
| WO | 2012012641 A1 | 1/2012 |
| WO | 2012045356 A1 | 4/2012 |
| WO | 2012061486 A2 | 5/2012 |
| WO | 2012064888 A2 | 5/2012 |
| WO | 2012083045 A1 | 6/2012 |
| WO | 2012145356 A1 | 10/2012 |
| WO | 2012145362 A1 | 10/2012 |
| WO | 2012148745 A1 | 11/2012 |
| WO | 2012148747 A1 | 11/2012 |
| WO | 2012158662 A1 | 11/2012 |
| WO | 2012158737 A1 | 11/2012 |
| WO | 2012158738 A1 | 11/2012 |
| WO | 2012158740 A1 | 11/2012 |
| WO | 2012158931 A1 | 11/2012 |
| WO | 2013063227 A1 | 5/2013 |
| WO | 2013081659 A1 | 6/2013 |
| WO | 2015099977 A1 | 7/2015 |
| WO | 2017123853 A1 | 7/2017 |

OTHER PUBLICATIONS

Badawi et al, "A Simple Percutaneous Technique for Hemostasis and Closure after Transcatheter Aortic Valve Implantation", Catheterization and Cardiovascular Interventions, Jan. 1, 2012, 79(1), 152-155.

Bui et al, "Double-Wire Angio-Seal Closure Technique after Balloon Aortic Valvuloplasty", Catheterization and Cardiovascular Interventions, 2010, 75, 488-492.

Extended European Search Report and Opinion dated Jun. 16, 2021 in EP Application No. 21163623.8.

Extended European Search Report dated Sep. 6, 2021 in EP Application No. 21166157.4.

(56) References Cited

OTHER PUBLICATIONS

International Search Report and Written Opinion for International Application No. PCT/US2012/061855 dated Jan. 22, 2013 (21 pages).
Koh, Wui-Jin et al. "Femoral vessel depth and the implications for groin node radiation," 1993, International Journal of Radiation Oncology 'Biology' Physics, vol. 27, p. 969-974.
PCT International Preliminary Report on Patentability, PCT/US2014/068694, dated Jun. 28, 2016, 11 pp.
PCT International Search Report and the Written Opinion, PCT/US2014/068694, dated Mar. 17, 2015, 17 pp.
PCT International Search Report dated Oct. 22, 2021 in PCT/US2021/041730.
PCT Written Opinion dated Oct. 22, 2021 in PCT/US2021/041730.
U.S. Appl. No. 61/352,807, filed Jun. 8, 2010, Walters.

\* cited by examiner

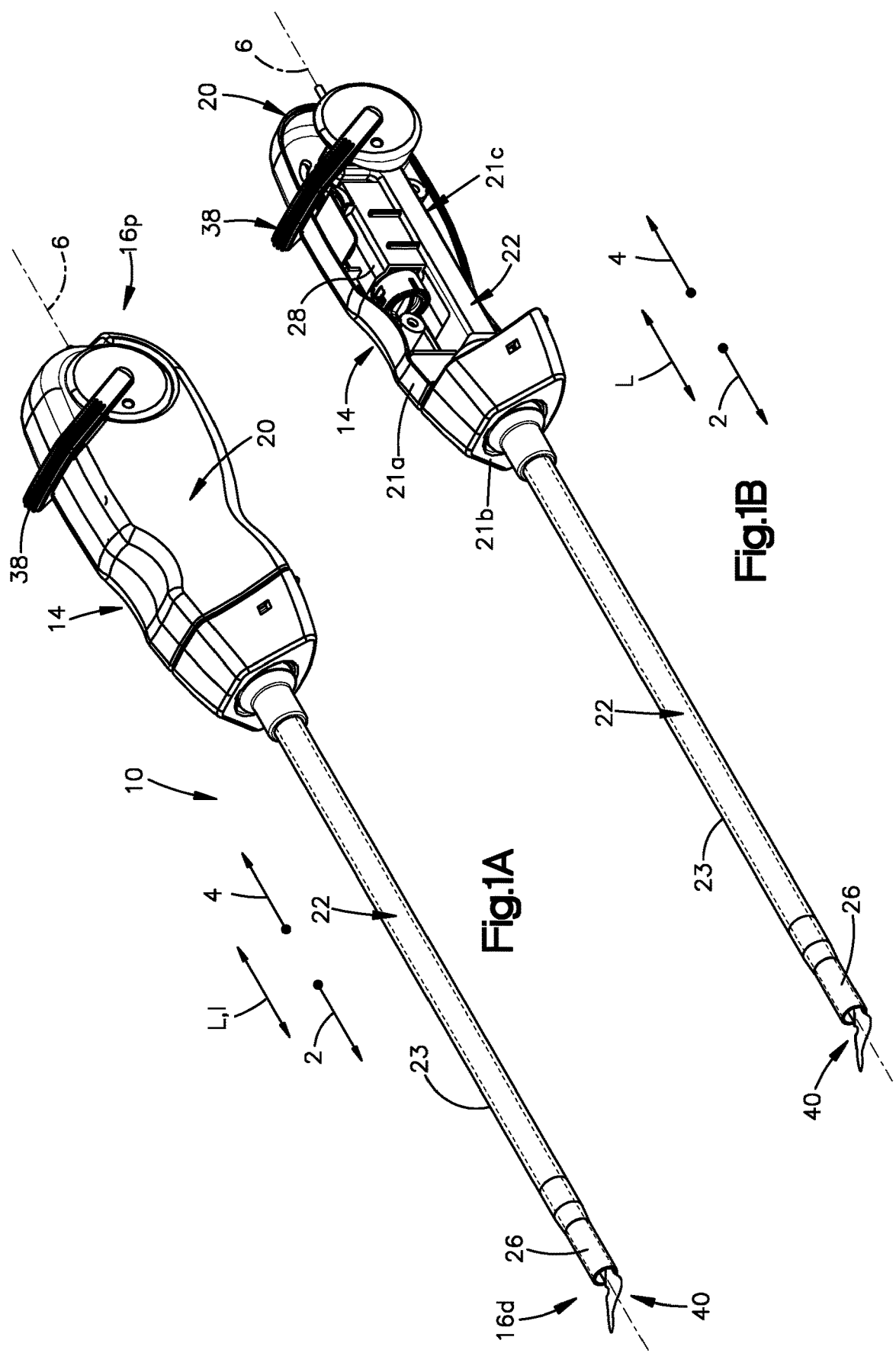

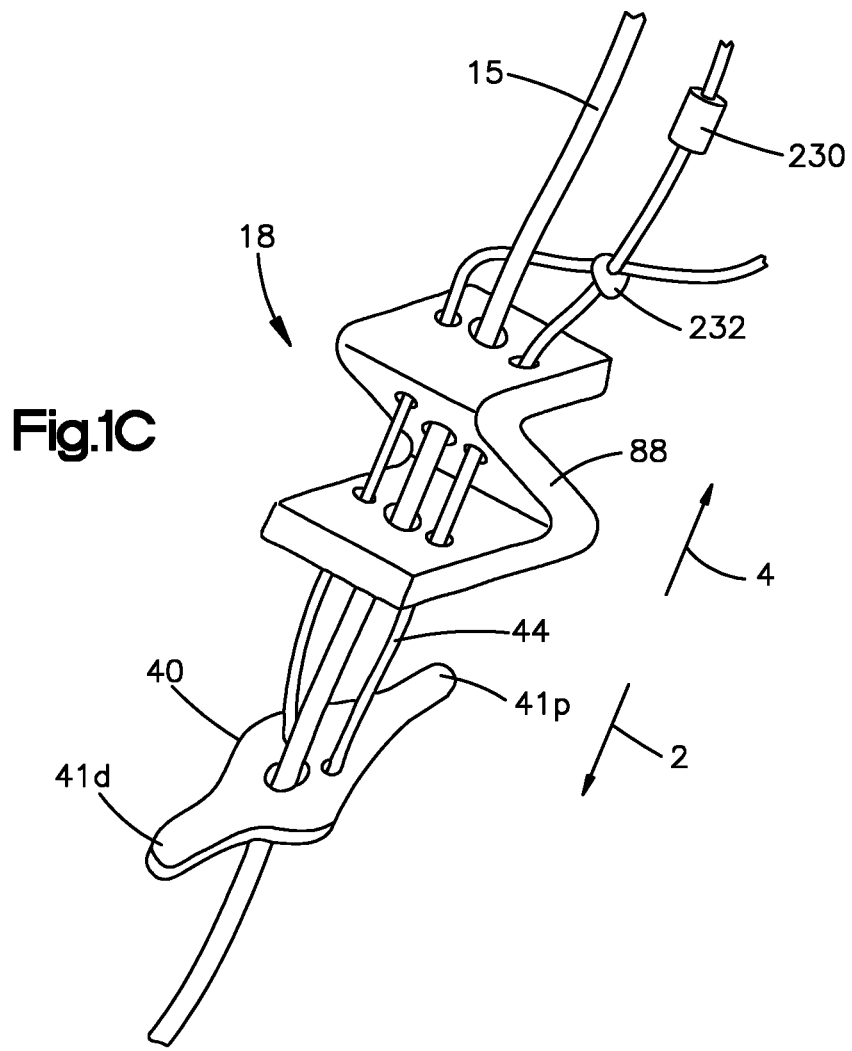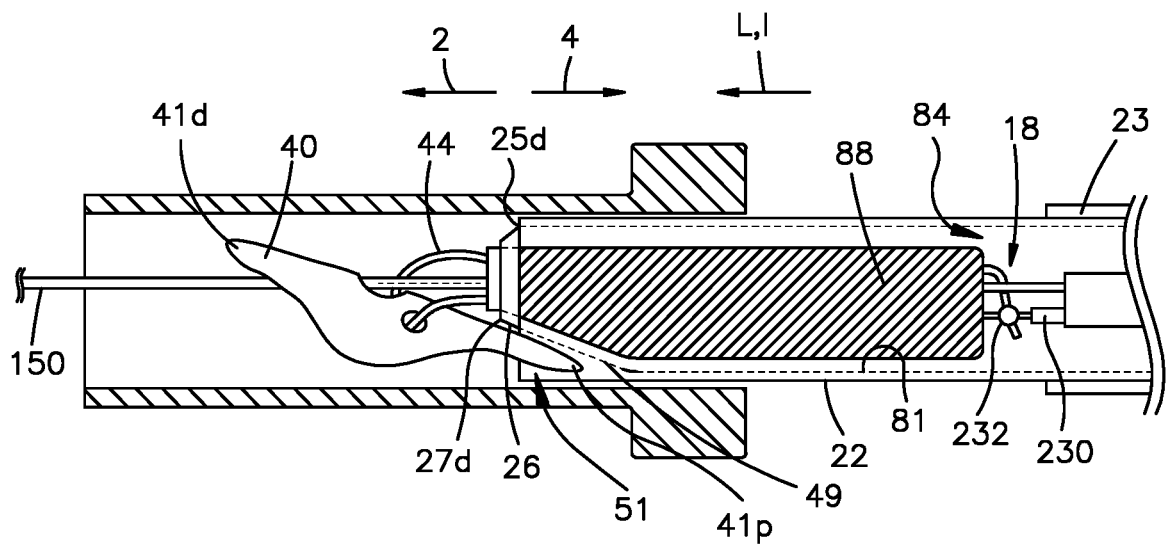

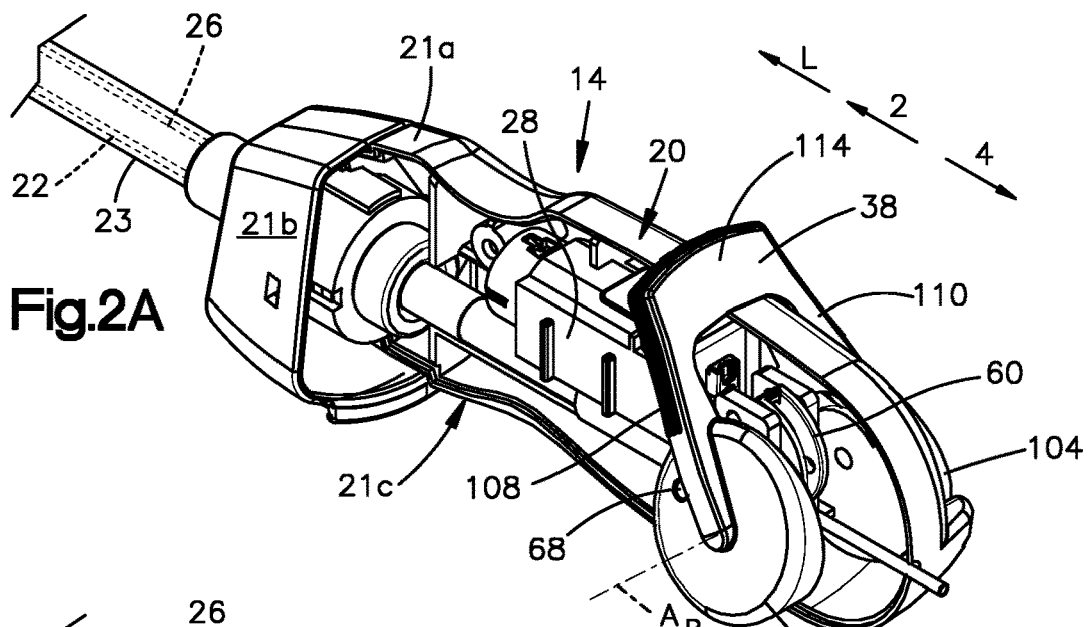
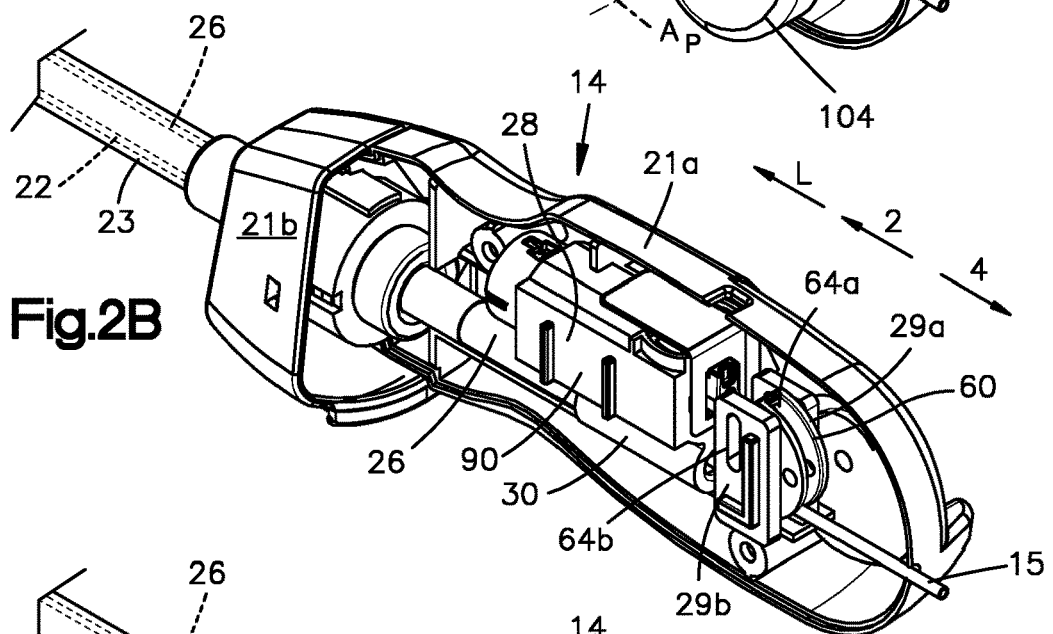
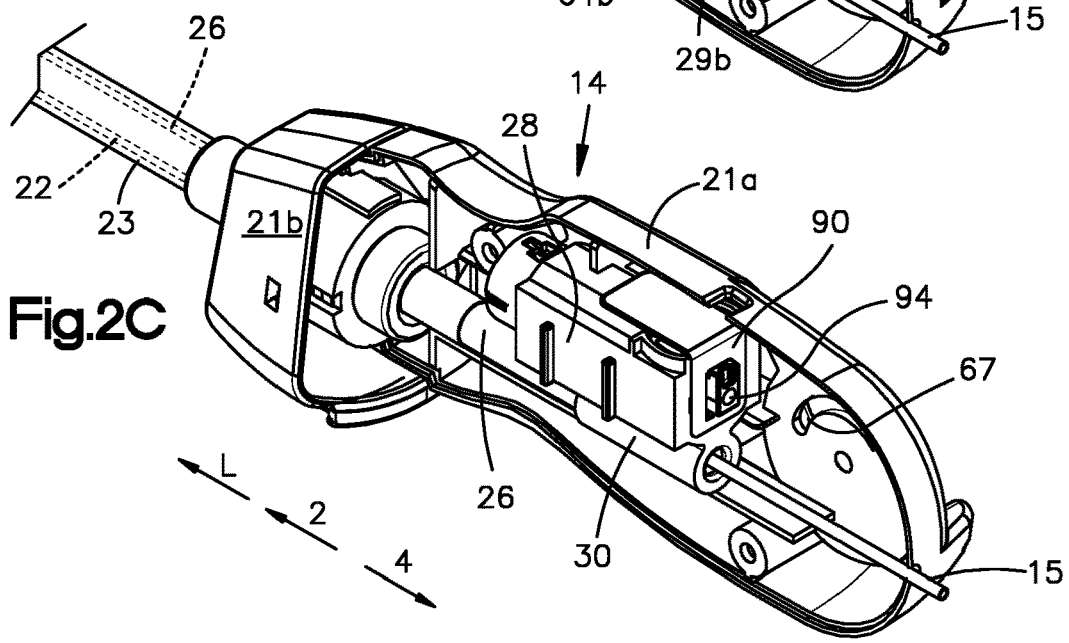

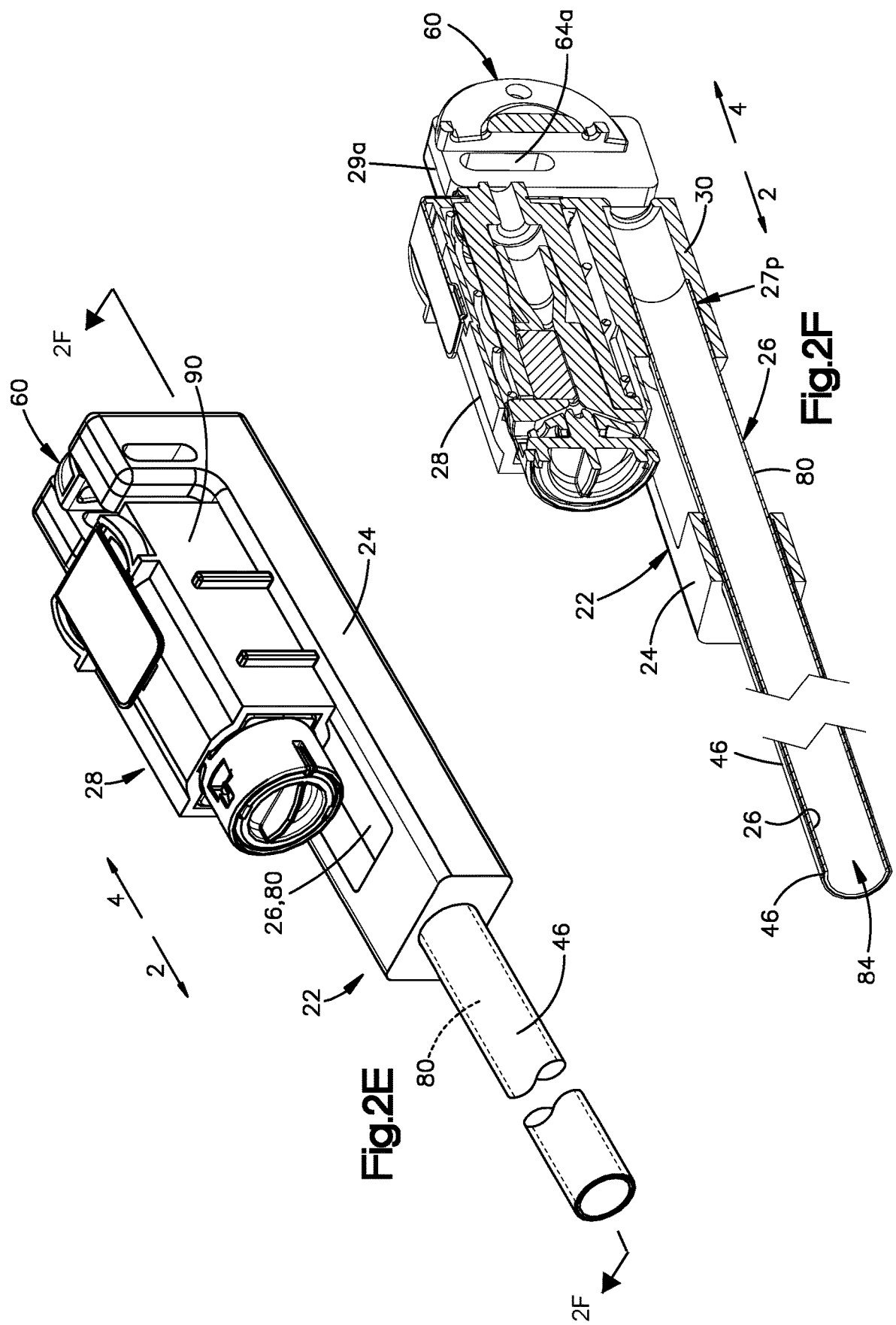

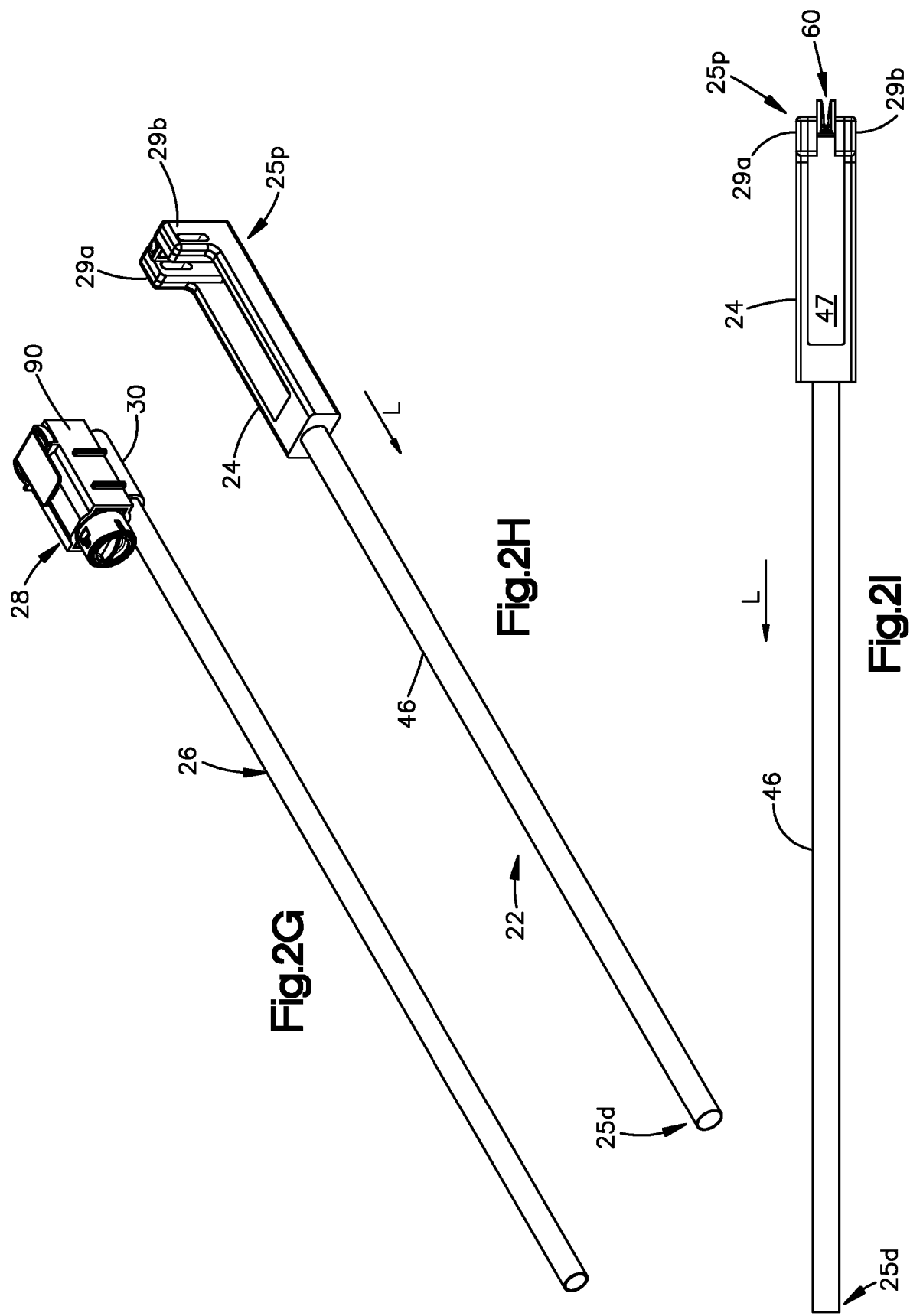

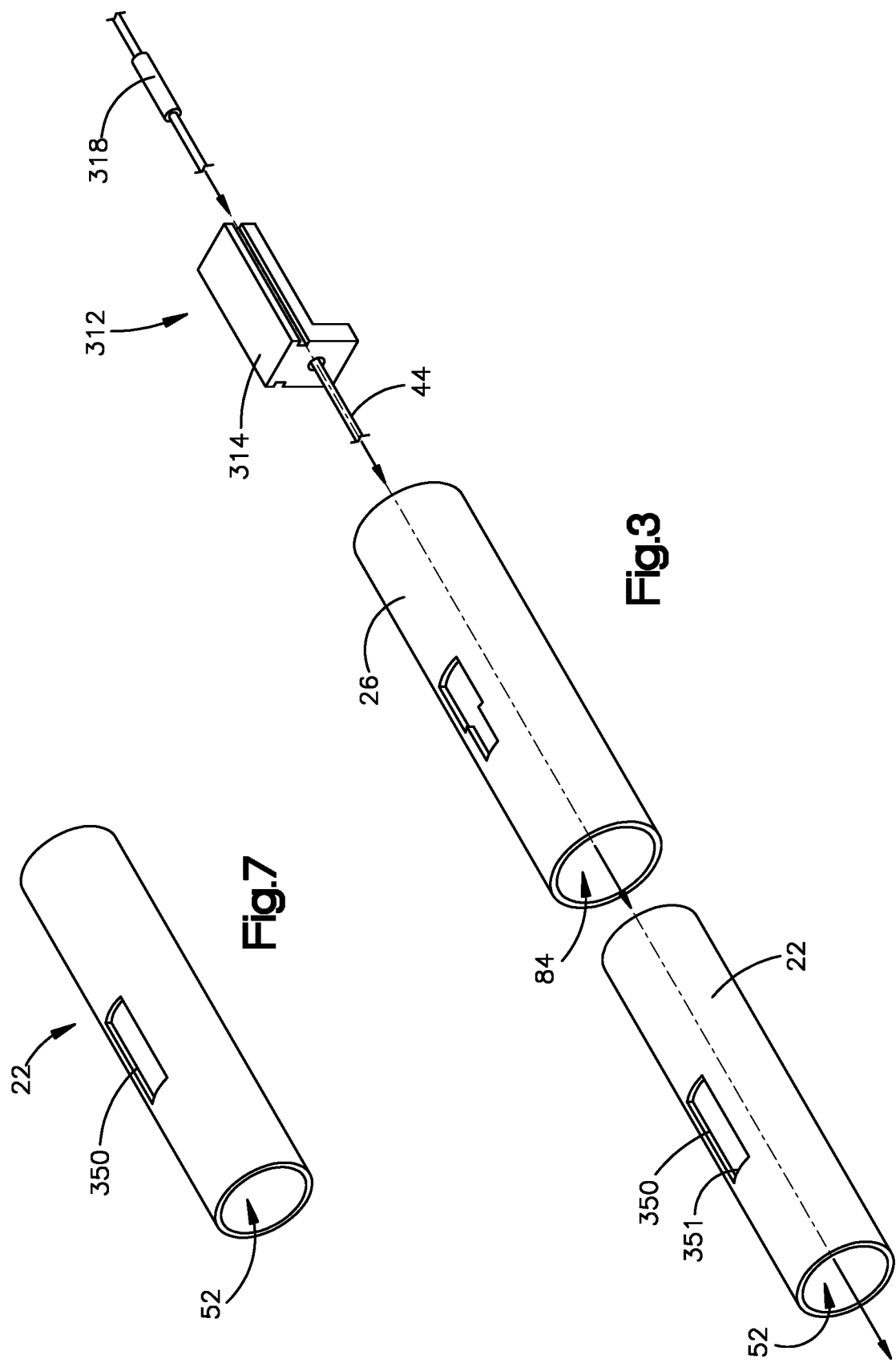

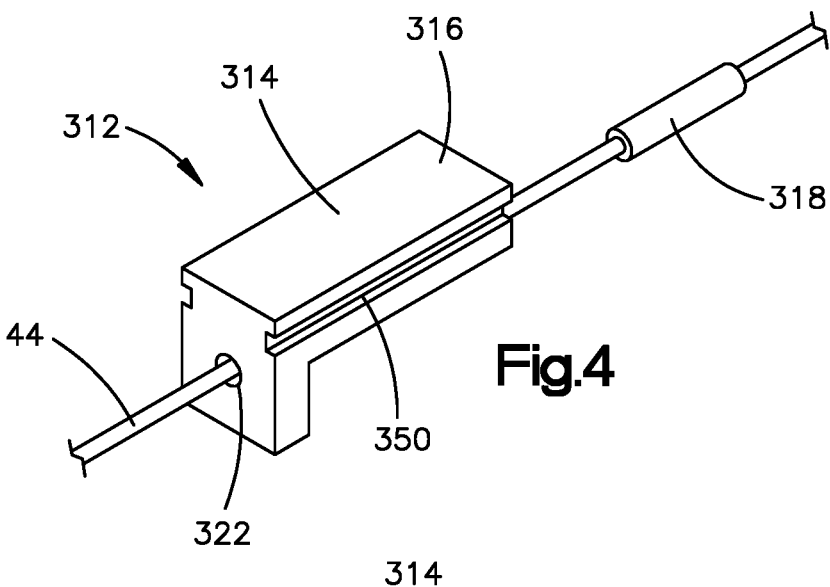
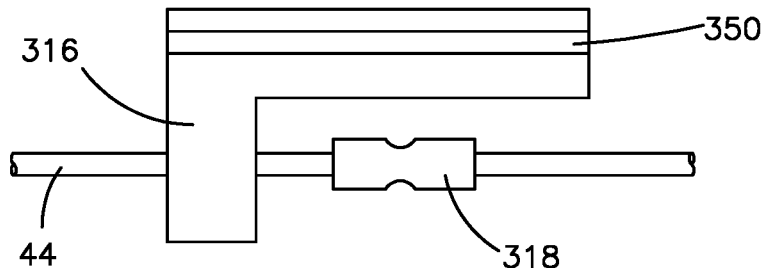
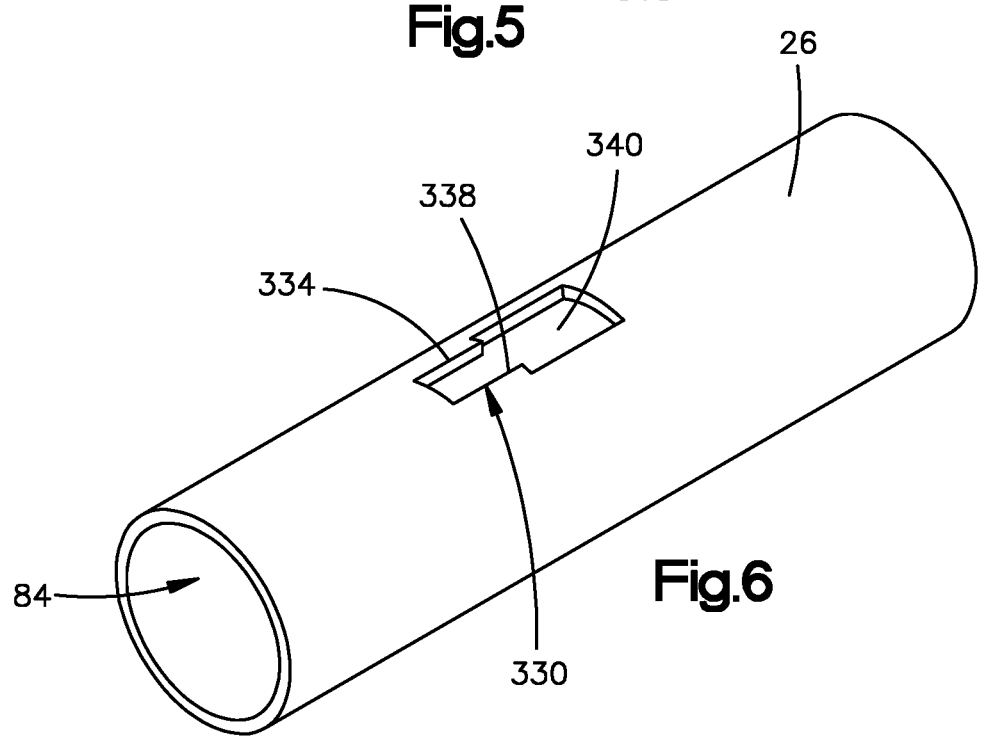

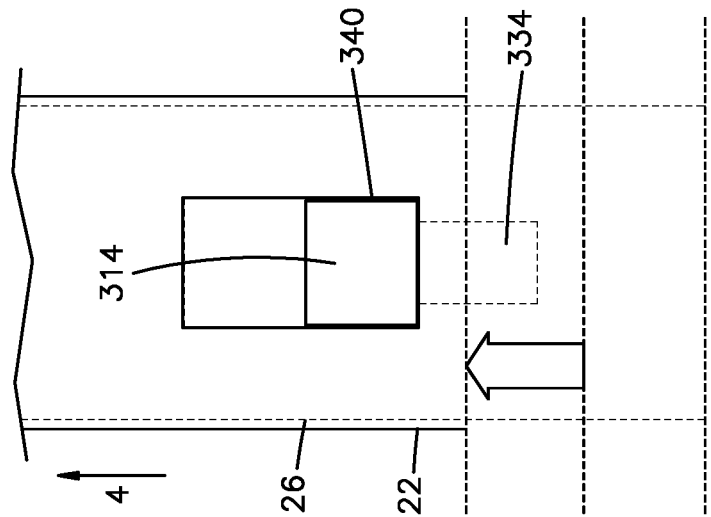
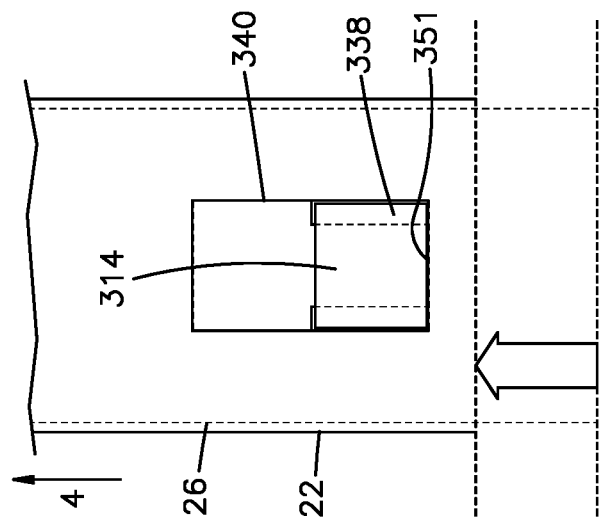
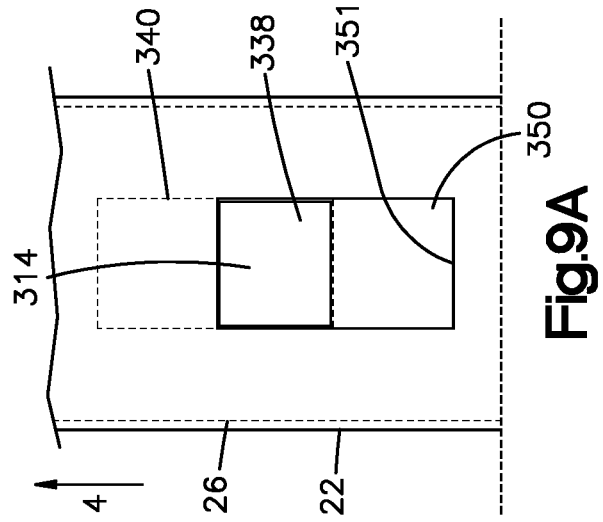

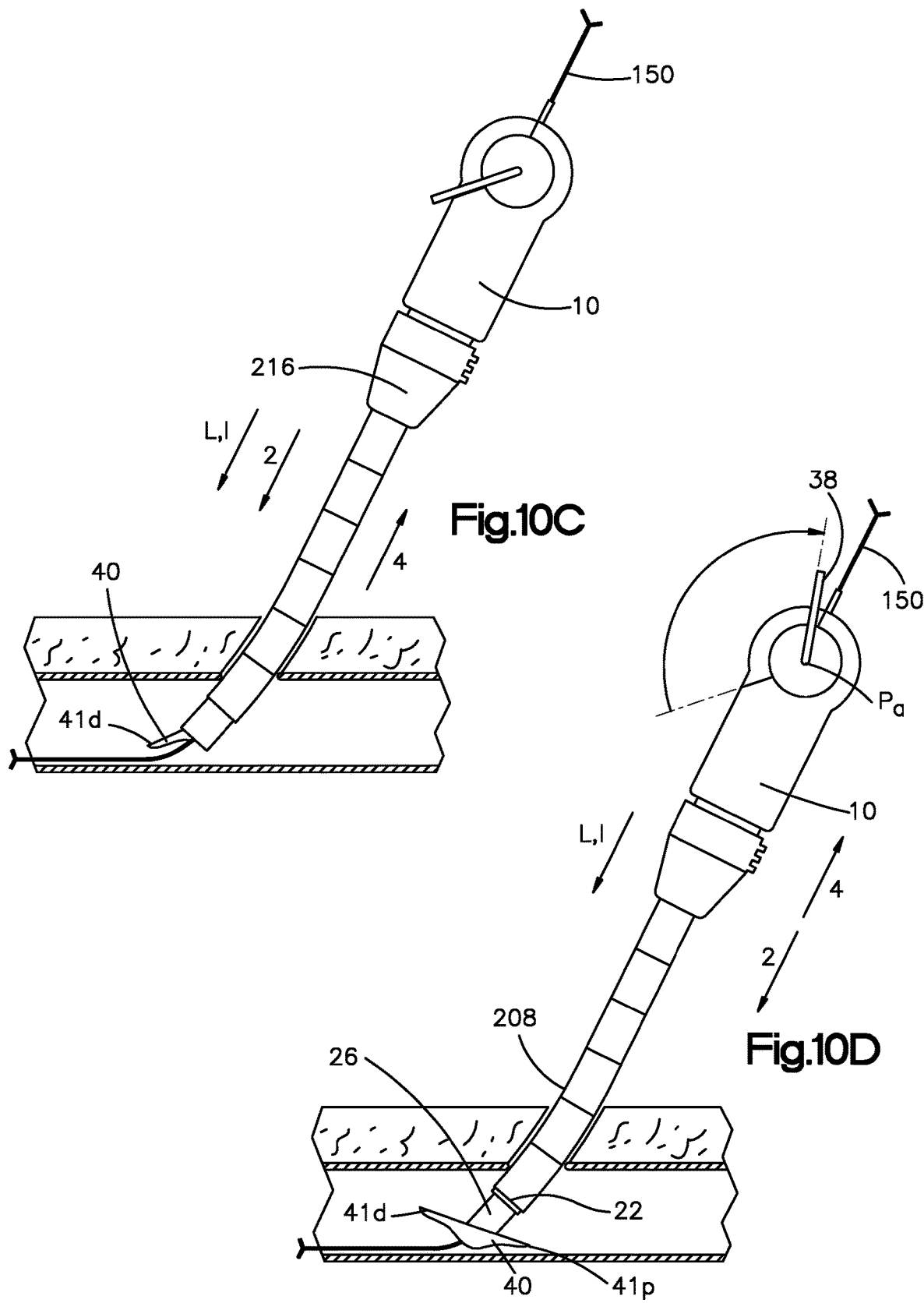

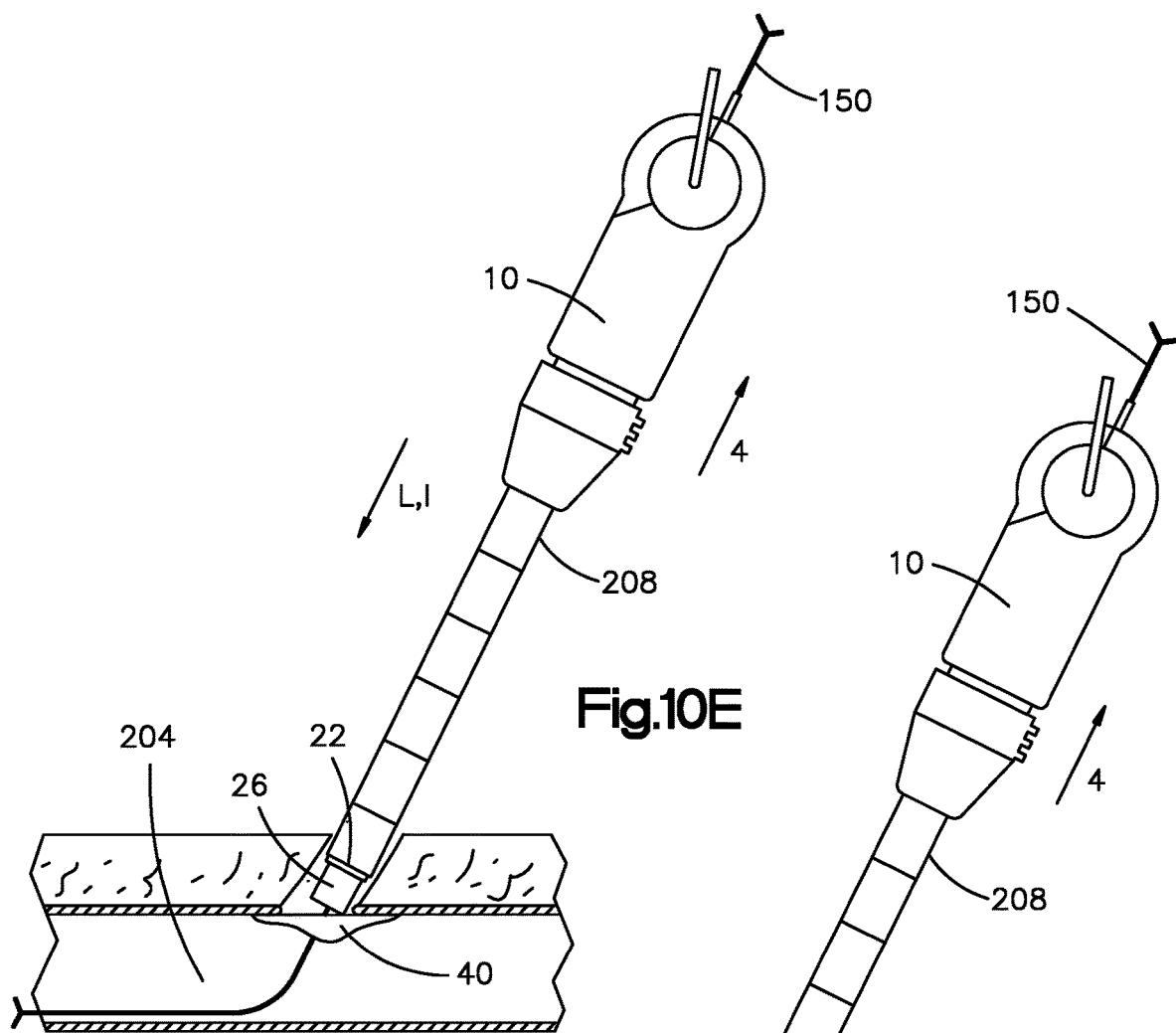

VASCULAR CLOSURE DEVICE

CROSS REFERENCE TO RELATED APPLICATIONS

This application is a continuation application of and claims the benefit of U.S. application Ser. No. 16/568,588, entitled "VASCULAR CLOSURE DEVICE" filed on Sep. 12, 2019, now U.S. Pat. No. 11,364,024,which is a divisional application of and which claims the benefit of U.S. application Ser. No. 15/105,180, entitled "VASCULAR CLOSURE DEVICE" filed on Jun. 16, 2016, now U.S. Pat. No. 10,448,937, which is a National Stage Application filed under 35 U.S.C. 371 of International Application Serial No. PCT/US2014/068694, filed on Dec. 5, 2014, which claims priority under 35 U.S.C. § 119(e) to U.S. Provisional Application Ser. No. 61/920,207, filed on Dec. 23, 2013, which are herein incorporated by reference in their entirety.

BACKGROUND

Percutaneous access of the vascular system for vascular device delivery is a common medical procedure. Typically, this involves using a hollow needle to puncture a vessel, then introducing an introducer sheath to open the puncture site for the introduction of catheters and wire guides for navigation through the vascular system to facilitate delivery. For example, in many cases, vascular access requires introduction of catheters and wire guides through the femoral artery. Once the procedure is completed, the devices are removed from the patient and pressure is applied to the puncture site to stop the bleeding. Thereafter, the puncture may be sealed using a closure device.

Closure devices generally consist of three basic sealing components: a toggle (or anchor) member, a sealing member (or plug), and a filament (or suture). To lock the components together within the puncture, a locking member may be used.

SUMMARY

A vascular closure device in accordance with an embodiment can include a release component, a delivery component, a sealing device and at least one actuator. The release component is elongate along a longitudinal direction, and can define a distal end and a proximal end. The delivery component can extend along the release component such that at least the release component is movable relative to the delivery component. The delivery component can include a delivery tube body and can define a delivery tube channel. The sealing device can have a toggle that is at least partially disposed within the release tube, a suture that is attached to the toggle and extends through the delivery tube channel, and a plug that is attached to the suture proximal to the toggle. The actuator can be coupled to the release component and is in communication with the suture such that actuation of the actuator causes (i) the release component to move the proximal direction relative to the delivery component so as to release the toggle from the release component, and (ii) the suture to be pulled in a proximal direction to thereby place the filament in tension and urge the toggle against a distal end of the delivery component such that the toggle is oriented in a sealing position.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and systems shown. In the drawings:

FIG. 1A is a perspective view of a vascular closure device in accordance with an embodiment of the present disclosure;

FIG. 1B is a partial cut-away view of the vascular closure device shown in FIG. 1A;

FIG. 1C is a perspective view of a sealing device associated with the vascular closure device in FIG. 1A;

FIG. 1D is a partial sectional view showing the sealing device shown in FIG. 1C disposed in a distal end of the vascular closure device shown in FIG. 1A;

FIGS. 2A-2C are rear perspective views of the vascular closure device with portions of the device removed for clarity;

FIG. 2E is a perspective view of the release component, delivery component and tensioner of the vascular closure device shown in FIG. 1A;

FIG. 2F is a perspective cross-sectional view of the release component, delivery component and a tensioner of the vascular closure device shown in FIG. 2E, taken along line 2-4;

FIG. 2G is a perspective view of the delivery component and tensioner of the vascular closure device shown in FIG. 2E;

FIGS. 2H and 2I are perspective and top views, respectively, of the release component of the vascular closure device shown in FIG. 1A;

FIG. 3 is a perspective exploded view of a tensioning mechanism for a vascular closure device in accordance with another embodiment of the present disclosure;

FIG. 4 is a schematic perspective view showing a portion of the tensioning element coupled to the suture;

FIG. 5 is a side view of the portion of the tension element shown in FIG. 4;

FIG. 6 is a partial perspective view of a delivery component configured to receive the portion of the tension mechanism shown in FIGS. 4 and 5;

FIG. 7 is a partial perspective view of a release component configured to receive the portion of the tension element shown in FIGS. 4 and 5;

FIG. 9A is a top plan view of the tensioning element in the first position;

FIG. 9B is a top plan view showing the release component moved proximally and abutting the tensioning element;

FIG. 9C is a top plan view showing the release component moved further proximally relative to that shown in FIG. 9B;

FIG. 10C is a schematic showing the access sheath and closure device combination pulled in a proximal direction such that the toggle is proximate to the puncture site;

FIG. 10D is a schematic showing actuation of the actuator to release the toggle and apply a tension to a filament;

FIG. 10E is a schematic showing the deployment device being pulled in a proximal direction such that the toggle abuts the vessel wall;

FIG. 10F is a schematic showing deployment of a plug of the closure device;

DETAILED DESCRIPTION OF ILLUSTRATIVE EMBODIMENTS

Figure 2D:
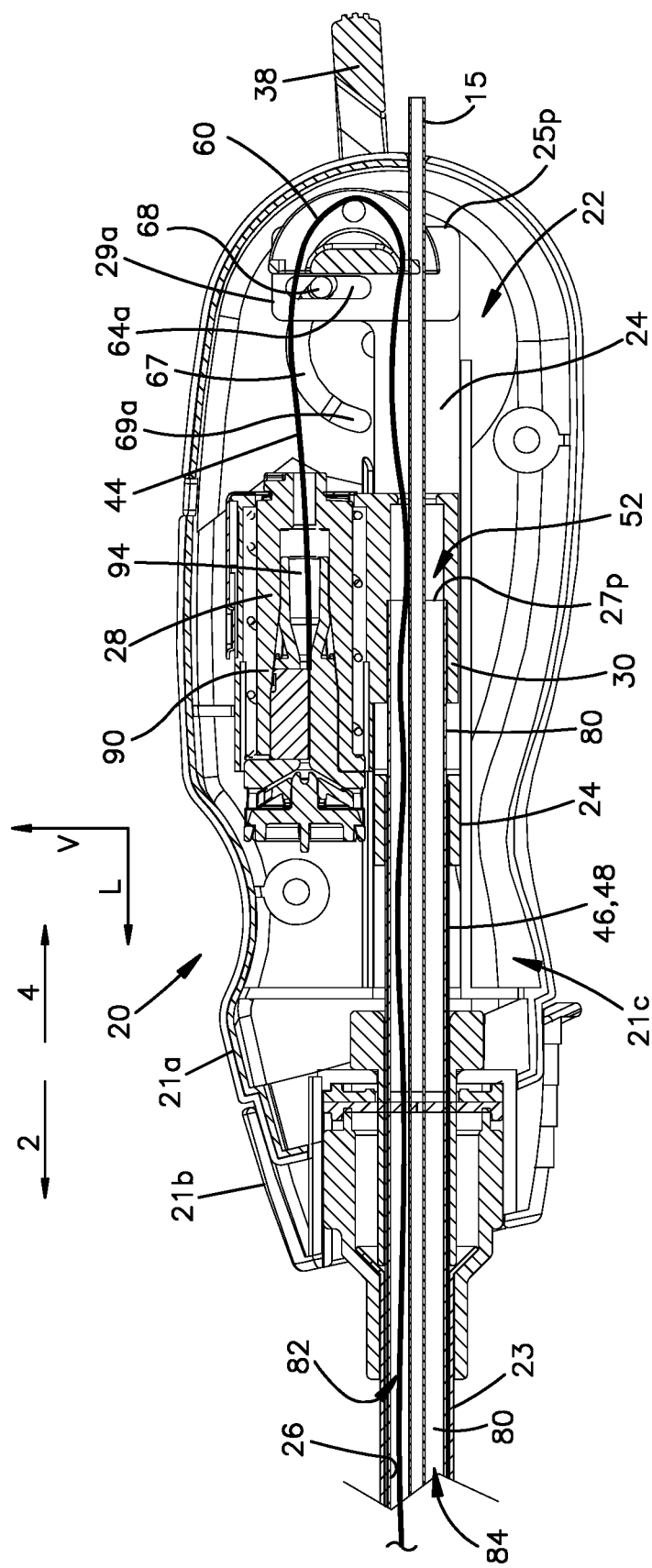
FIG. 2D is a cross-sectional view of the vascular closure device shown in FIG. 2A, taken along line 2D-2D.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIG. 1A-1D, a vascular closure device 10 in accordance with an embodiment of the present disclosure can include a sealing device or implantable unit 18 at least partially disposed within a deployment device 14. The vascular closure device 10 can be configured such that after the deployment device 14 is inserted into a vessel through a puncture site of the vessel, the sealing device 18 is deployed to thereby seal or otherwise close the puncture site of the vessel. The deployment device 14 is configured to control orientation of a toggle 40 of the sealing device 18 in an easier and more efficient manner during deployment of the sealing device 18. In accordance with the illustrated embodiment, the deployment device 14 includes a release component 22 (shown in dashed lines in FIGS. 1A and 1B) that restrains the toggle 40, a delivery component 26 (also shown in dashed lines in FIGS. 1A and 1B) that contains at least a portion of the toggle 40 and a suture 44 of the sealing device 18, and one or more actuators 38 coupled to the release component 22. The release component 22 is operatively associated with the suture 44 such that actuation of the actuator 38 causes the release component 22 to 1) release the toggle 40, and 2) apply tension to the suture 44, which urges the toggle 40 against the delivery component 26 and orients the toggle 40 in the sealing position.

Turning to FIG. 1C, the sealing device 18 includes the toggle 40 connected to the suture 44, a plug 88 coupled to the suture 44 and spaced from the toggle 40 in a proximal direction 4, and a locking member 230 proximal to the plug 88. The toggle 40 includes a distal end 41d and a proximal end 41p opposed to the proximal end 41p, and a plurality of apertures (not numbered) extending therethrough. The suture 44 is extends through the apertures as illustrated such that an end of the suture 44 is formed into a slidable knot 232. The knot 232 is slidable along the suture 44 between the plug 88 and the locking member 230. In an implanted state, the toggle 40 is adjacent an inner surface of the vessel and the locking member 230 squeezes the toggle 40 and the plug 88 against the outer surface vessel to seal the puncture. A guide lumen 15 extends through the sealing device 18 and is configured to receive a guide wire 150 as will be discussed below.

The sealing device 18 is formed with materials suitable for surgical procedures. For instance, the toggle 40 can be made of any biocompatible material. For example, the toggle 40 can be made of a polylactic-coglycolic acid or other synthetic absorbable polymer that degrades in the presence of water into naturally occurring metabolites. In other embodiments, the toggle can be made of stainless steel, biocorrodible iron, and biocorrodible magnesium. It should be appreciated, however, that the toggle 40 can be made of other materials and can have other configurations so long as it can be seated inside the vessel against the vessel wall. The plug 88 can comprise a strip of compressible, resorbable, collagen foam and can be made of a fibrous collagen mix of insoluble and soluble collagen that is cross linked for strength. It should be appreciated, however, that the plug member 88 can have any configuration as desired and can be made from any material as desired. The suture 44 can be any elongate member, such as, for example a filament, thread, or braid.

Referring again to FIGS. 1A, 1B and 1D, the deployment device 14 is elongate along a longitudinal direction L and includes a proximal end 16p and a distal end 16d spaced from the proximal end 16p along an axis 6 that is aligned with the longitudinal direction L. The longitudinal direction L can include and define a distal direction 2 that extends from the proximal end 16p toward the distal end 16d. Further, the longitudinal direction L can include and define a proximal direction 4 that is opposite the distal direction 2 and that extends from distal end 16d toward the proximal end 16p. The deployment device 14 is configured to insert the toggle 40 into the vessel along an insertion direction I (see FIG. 4). The longitudinal direction L can be aligned with the insertion direction I during a portion of the sealing procedure.

Turning to FIGS. 1A and 1B, in accordance with the illustrated embodiment, the deployment device 14 includes a handle member 20, the release component 22 supported by the handle manner 20 and extending from handle member 20 in the distal direction 2, the delivery component 26 also supported by the handle member 20 and extending along the distal direction 2, and a tensioner 28 supported by the handle member 20 and positioned adjacent to the release component 22. A portion of delivery component 26 is shown in dashed lines in FIGS. 1A and 1B. The actuator 38 is coupled to both the handle member 20 and the release component 22. As noted above, the actuator 38 is configured to 1) cause the release component 22 to move in the proximal direction 4 from a first or initial position relative to the delivery component 26 into a second or releasing position relative to the delivery component 26, and 2) apply a tensile force to the suture 44 during or subsequent to movement of the release component 22 from the initial position into the release position. The description below refers to the release component 22 being moveable relative to the delivery component 26. But the deployment device 14 can be configured so that the delivery component 26 is moveable relative to the release component 22. The deployment device 14 also includes the guide lumen 15 that extends through the deployment device 14, and an optional outer sheath 23 that contains and supports portions of the release component 22 and delivery component 26.

Continuing with FIGS. 1A and 1B, the handle member 20 includes a housing 21a, a sheath hub 21b and a cavity 21c defined at least partly by housing 21a and sheath hub 21b.

Figure 10A:
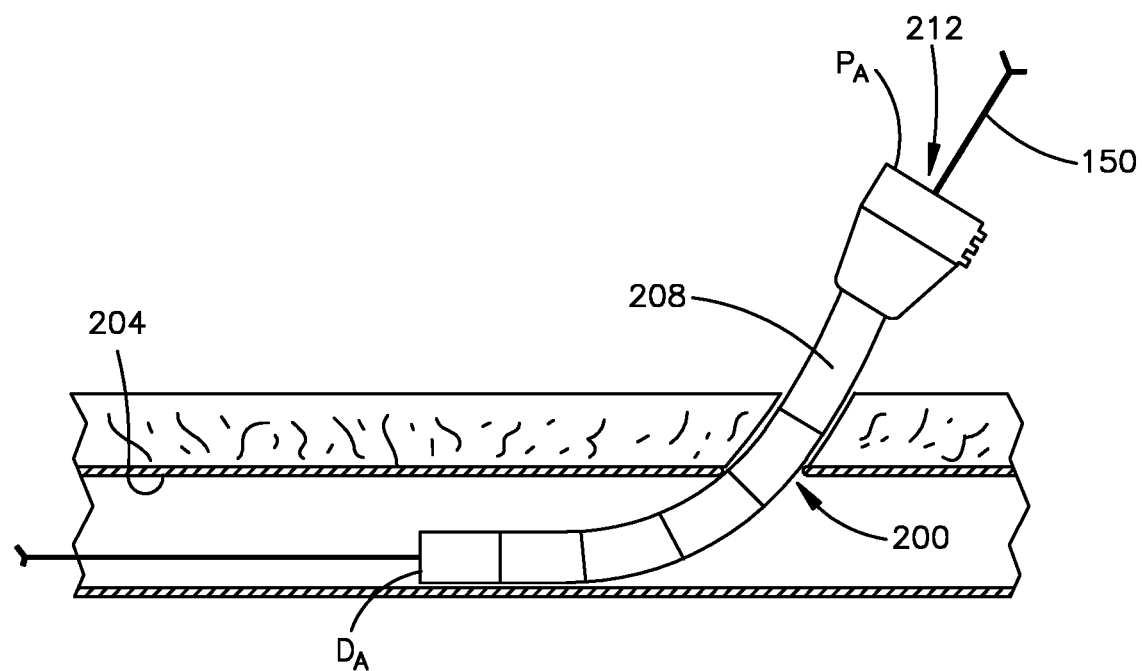
FIG. 10A is a schematic showing an access sheath partially disposed within a vessel through a puncture site in the vessel.

The cavity 21c is sized to contain a portion of the release and delivery components 22 and 26 and the tensioner 28. The optional outer sheath 23 extends from the sheath hub 21b in the distal direction 2 along the release and delivery components 22 and 26. The sheath hub 21b mates the access sheath 208 (FIG. 10A).

Turning to FIGS. 1B, 2H and 2I, the release component 22 is elongate along a first or longitudinal direction L defines a distal end 25d and a proximal end 25p spaced from the distal end 25d along the longitudinal direction L. In accordance with the illustrated embodiment, the release component 22 includes a release hub 24 and a release tube 46 that is fixed to the release hub 24 extends from the release hub 24 in the distal direction 2. The release hub 24 includes a pair of tabs 29a, 29b disposed at the proximal end 25p of the release component 22. A pulley 60 is coupled to the tabs 29a, 29b and defines a curved track that receives the suture 44 as will be explained below. The hub 24 defines a slot 47 that is elongate along the longitudinal direction L and is aligned with the release tube 46. The slot 47 is sized to receiver a coupler 30 of the tensioner 28.

Referring to FIGS. 2D-2F, the release tube 46 includes a release tube body 48 that is elongate along the longitudinal direction L. The release tube body 48 defines a release tube channel 52 (FIGS. 2D, 2F) that extends along the longitudinal direction L from the hub 24 toward the proximal end 25p. In the illustrated embodiment, the release tube channel 52 (FIG. 2D) extends completely through the release tube body 48 from the hub 24 to the distal end 25d. Furthermore, in the illustrated embodiment the release tube body 48 is cylindrical such that the release tube channel 52 is radially enclosed. It should be appreciated, however, that the release tube channel 52 can extend partially through the release tube body 48 as desired and that the release tube body 48 can have other configurations as desired. For example, the release tube body 48 can be U-shaped such that the release tube channel 52 is partially radially open. As best shown in FIG. 2F, the release tube channel 52 is sized to slidably receive a portion of the delivery component 26 such that the release component 22 is movable relative to the delivery component 26.

Referring FIGS. 2A, 2B, 2D, and 2I, the pulley 60 is disposed at the proximal end 25p of the release component 22. As shown, the suture 44 extends around the pulley 60 along the guide track and into the tensioner 28. As the release component 22 is pulled in the proximal direction 4, the pulley 60 pulls the suture 44 in proximal direction 4 thereby applying a tensile force to the toggle 40. In such an embodiment, the tensioner 28 is positioned alongside the release component 22. It should be appreciated, however, that in some embodiments, the tensioner 28 is positioned proximal to the release tube and is in-line with the release component 22 such that the suture 44 extends through the release tube and into the tensioner 28 along the first direction L.

With continued reference to 2A, 2B, 2D, and 2I, the release component 22 can include at least one mating member 64 that mates with a corresponding mating member 68 of the actuator 38 to thereby transfer the motion of the actuator 38 to the release component 22. In the illustrated embodiment, the release component mating member 64 is a pair of slots 65a and 65b defined by the respective pair of tabs 29a and 29b. Each slot 65a and 65b is elongate along a direction a vertical direction V that is perpendicular to the first direction L. The actuator 38 mating member 68 can be operatively engaged with elongate slots 65a and 65b of release component 22 such that actuation of the actuator 38 causes the release component 22 to translate along the first direction L. It should be appreciated, however, that the mating member 64 can have any configuration as desired. For example, the mating member 64 can be bore having a diameter that is equal to that of the pin such that translation of the actuator 38 along the first direction L causes the release component 22 to translate along the first direction L.

As shown in FIGS. 1B, 2D-2G, the delivery component 26 is coupled to the tensioner 28 and extends along the release component 22 toward the distal end 16d of the deployment device 14. In accordance with the illustrated embodiment, because the tensioner 28 is fixed to the housing 21a, the delivery component 26 is fixed to the housing 21a and thus the handle member 31. The delivery component 26 includes a delivery tube body 80 that is elongate along the first direction L and defines a distal end 27d and a proximal end 27p spaced from the distal end 27d in the first direction L. The delivery tube body 80 defines an inner surface 81, which in turns defines a delivery tube channel 84 that extends at least partially through the delivery tube body 80 along the first direction L. As illustrated embodiment, the delivery tube channel 84 extends completely through the delivery tube body 80 from the proximal end 27p to the distal end 27d. However, the channel 84 can extend along a portion of the delivery tube body 80. Furthermore, in the illustrated embodiment the delivery tube body 80 is cylindrical such that the delivery tube channel 84 is radially enclosed. It should be appreciated, however, that the delivery tube channel 84 can extend partially through the delivery tube body 80 as desired and that the delivery tube body 80 can have other configurations as desired. For example, the delivery tube body 80 can be U-shaped such that the delivery tube channel 84 is partially radially open. As illustrated, the proximal end 27p of delivery component is fixed to the tensioner 28 and the distal end 27d of delivery component is configured to hold at least a portion of the sealing device 18 (FIG. 1D).

The delivery tube channel 84 is sized to retain at least a portion of the sealing device 18. In particular, the plug 88 and locking member 230 are retained within the delivery tube channel 84, while the toggle 40 is configured to be initially trapped between the delivery component 26 and the release component 22. For instance, the distal end 25d of the release tube 48 defines an offset surface 49, which can be angled with respect to the longitudinal axis 6. The offset surface 49 and inner surface 81 of the delivery tube 80 define a cavity 51 that receives the proximal end 41p of the toggle 40 when release component 22 is in the initial position (as shown in FIG. 1D). The angle of the offset surface 49 can define the orientation of the toggle 40 in this initial position, whereby the distal end 41d of the toggle 40 is spaced some distance in the distal direction 2 beyond the distal ends 25d and 27d of the release and delivery components 22 and 26, respectively. The suture 44 extends from the toggle 40 through the delivery tube channel 84, through the proximal end 27p (FIG. 2D) around the pulley 60 along the guide track and is coupled to the tensioner 28. The guide lumen 15 extends through the channel 84 and exits the distal end 16d of the vascular closure device 10. When the actuator 38 is actuated as will be further detailed below, the release component 22 moves in the proximal direction 4 thereby releasing the proximal end 41p of the toggle 40 from between the release component 22 and the delivery component 26. As the release component 22 moves in the proximal direction 4, the suture 44 will be pulled in the proximal direction 4 to thereby place the suture 44 in tension and urge the toggle 40 against the distal end 27d of the delivery component 26. At this point, the toggle 40 is oriented in the sealing position (see FIG. 10D). In the sealing position, the toggle 40 has been repositioned so that the toggle 40 is placed against the distal end 27*d* of the delivery component 26 and is oriented more transversely with respect to the axis 6 compared to the position when the toggle 40 is restrained by the release component 22.

As shown in FIGS. 2D-2G, the tensioner 28 is disposed on the delivery component 26 and is positioned alongside the release component 22 so as to receive the suture 44 as noted above. In accordance with the illustrated embodiment, the tensioner 28 includes a tensioner housing 90, a coupler 30 that extends from the housing 90 and is attached to the delivery component 22, and a drag member 94 disposed within the tensioner housing 90. The suture 44 extends into the tensioner housing 90 through the drag member 94 and such that a frictional force is applied to the suture 44 by the drag member 94. The tensioner housing 90 coupled the housing 21*a* and fixed thereto. The coupler 30 as illustrated is a tubular component that receives the proximal end 2'7*p* of the delivery tube body 80. As illustrated, the delivery tube body 80 is fixed to the coupler 30 which indirectly fixes the delivery component 26 to the housing 21*a*. The suture 44 extends from the proximal end 2'7*p* of the delivery tube body 80, through the coupler 30, around the pulley 60 and into the drag member 94 and is spooled within the tensioner housing 90 (not shown). Spooling the suture 44 in tensions housing 90 allows suture 44 to dispense from the deployment device 14 when the deployment device 14 is pulled is proximal direction 2 to thereby deploy the sealing device 18 (see FIGS. 10E and 10F). The frictional force applied to the suture 44 by the drag member 94 can be high enough to maintain the suture 44 in tension after the actuator 38 has been actuated and the toggle 40 has been urged against the distal end 27*d* of the delivery component 26. At the same time the frictional force applied to the suture 44 by the drag member 94 can be low enough to allow the suture 44 to dispense from the tensioner housing 90 when the deployment device 14 is pulled in a proximal direction 4 relative to the toggle 40. In the illustrated embodiment, the drag member 94 is a silicon member that pinches the suture 44. The tensioner 90 and drag member 94 can be similar to the tensioner described in U.S. Patent Application Publication No. 2013/0178895. It should be appreciated, however, that the drag member 94 can have other configurations as desired.

Turning to FIGS. 2A-2D, the deployment device 14 can include one or more actuators that are configured to transition the release component 22 into a releasing position and to cause a tension to be applied to suture 44 when toggle 40 is released from the release component 22 as described above. As noted above, the actuator 38 can include the mating member 68 that operatively engages the mating member 64 of the release component 22 such that motion of the actuator 38 relative to the handle member 20 causes the release component to translate in the proximal direction 4 and further applies a tension to the filament. In accordance with the illustrated embodiment, the actuator 38 can be configured as a lever 100 that is rotatably coupled to the handle member 20. The actuator 38 or lever 100 can include a pair of side members 104 rotatably coupled to each side of the housing 21*a*, a first leg 108 that extends from one of the side members 104, a second leg 110 that extends from the other side member 104, and a transverse member 114 that connects the first leg 108 to the second leg 110. The actuator 38 is configured to pivot about a pivot axis $A_P$ that is perpendicular to the axis 6. The pivot axis $A_P$ may or may not intersect axis 6. The housing 21*a* defines a curved housing slot 67 that is curved with respect to the pivot axis $A_P$. The curved housing slot 67 has a first end 69*a* (FIG. 2D) and second end (not numbered) spaced apart from the first end along the proximal direction 4. The mating member 68 of the actuator 38 can be a pin 68 that is coupled to and extends between the side members 104 at a location that is offset from the pivot axis $A_P$. The pin 68 extends through curved housing slot 67 and through the elongate slots 64*a* and 64*a* of the hub 24 of the release component 22 such that the actuator 38 is operatively coupled to the release component 22. As the actuator 38 pivots about the pivot axis $A_P$, the pin 68 moves from the first end 69*a* the curved housing slot 67 toward the second end of the curved housing slot 67, and also moves along the slots 64*a* and 64*b* along the vertical direction V. Because the release component 22 is moveable relative to housing 21*a*, as pin 68 moves along the curved housing slot 67, the pin 68 advances the hub 24 of the release component 22 in the proximal direction 4. The result in accordance with the illustrated embodiment is that rotation of the actuator 38 causes the release component 22 to translate in the longitudinal direction L. It should be appreciated, however, that the actuator 38 can have other configurations as desired and is not limited to the disclosed lever.

In operation, the deployment device 14 is initially configured to insert the toggle 40 into the vessel. When the actuator 38 is actuated, the release component 22 moves in the proximal direction 4 relative to the delivery component 26 into the releasing position (not illustrated) thereby releasing the proximal end 41*p* of the toggle 40 from between the release component 22 and the delivery component 26. As the release component 22 moves in the proximal direction 4, the suture 44 will be pulled in the proximal direction 4 to thereby place the suture 44 in tension and urge the toggle 40 against the distal end 27*d* of the delivery component 26. At this point, the toggle 40 is oriented in the sealing position (see FIG. 10D). Accordingly, the release component 22 is configured to restrain the toggle 40 of the sealing device 18 during insertion of the vascular closure device 10 into the vessel and subsequently release the toggle 40 so that the toggle 40 can be oriented for the sealing procedure. The release component 22 is also in communication with the suture 44 via the pulley 60 such that when the actuator 38 is actuated, the release component 22 pulls the suture 44 in the proximal direction to thereby place the suture 44 in tension. Application of tension along the suture 44 urges the toggle 40 against the distal end 27*d* of the delivery component 26 and orients the toggle 40 into the sealing position. In the illustrated embodiment, the actuator 38 and release component 22 are configured such that continuous movement of the actuator 38 relative to the housing 21*a* will move the release component 22 in the proximal direction 4, thereby releasing the toggle 40 from the release component 22 and subsequently apply tension to the suture 44. It should be appreciated, however, that in some embodiments the suture 44 can be tensioned as the toggle 40 is being released. It should further be appreciated that in some embodiments, the device 14 can include a first actuator to release the toggle 40 and a second actuator that tensions the suture 44.

It should be appreciated, that the vascular closure device can include other configurations. For example, FIGS. 3-9C shows another configuration for tensioning the suture 44. The vascular closure device 310 shown in FIGS. 3-9C includes like features and operates in substantially a similar manner as the vascular closure device 10 shown in FIG. 1A-2I unless otherwise described. As shown in FIG. 3, a vascular closure device 310 in accordance with another embodiment, can include a tensioning element 312 that includes a shuttle 314 coupled to the suture 44 and an engagement member 318 (illustrated as a crimp) coupled to the suture 44 proximal to the shuttle 314. Tensioning element initially coupled to the delivery component 26 and can be decoupled from the delivery component 26 and upon actuation of the release component 22 as described above. More specifically, the shuttle 314 is configured to be initially coupled to the delivery component 26 and upon actuation of the release component 22, the shuttle 314 and crimp 318 are configured to tension the suture 44 via the actuator 38 described above.

As shown in FIGS. 4 and 5, the shuttle 314 includes a shuttle body 316 and defines a channel 322 that extends through the shuttle body 316 and is sized to receive the suture 44 such that the shuttle 314 can slide along the suture 44 and is further sized to receive the crimp 318 to thereby fix the shuttle 314 to the suture 44 so that the filament can be tensioned as the release component 22 is pulled proximally. As shown in FIGS. 4 and 5, the shuttle 314 further defines a pair of opposed recesses 326 that extend into the shuttle body 316 and along the shuttle body 316. The recesses 326 are configured to mate with portions of the delivery tube to thereby couple the shuttle 314 to the delivery tube.

Now in reference to FIG. 6, the delivery component 26 defines a slot 330 that extends through the delivery tube body and into the delivery tube channel 84. The delivery component slot 330 defines a guide portion 334 having a pair of guides 338 configured to be received by the recesses 326 of the shuttle 314 such that the shuttle 314 can translate along the guides 338 as the shuttle 314 is moved proximally by the release component 22. The delivery component slot 330 further defines a drop portion 340 proximal to the guide portion 334 that is sized to receive the shuttle 314 from the guides 338 such that the shuttle 314 moves into or otherwise drops into the delivery tube channel 84.

As shown in FIG. 7, the release component 22 also defines a slot 350 that extends through the release tube body 48 and into the release tube channel 52. The release tube body 48 defines a distal edge 351 defining the distal end of the slot 350. The slot 350 is configured to align with the slot 330 of the delivery component 26 and is sized similarly as the drop portion 340 of the slot 330. As shown in FIGS. 8A-8C and 9A-9C, the shuttle 314 extends through the aligned slots 330 and 350 such that movement of the release component 22 proximally causes the release tube body to abut and pull the shuttle 314 proximally.

Figure 8A:
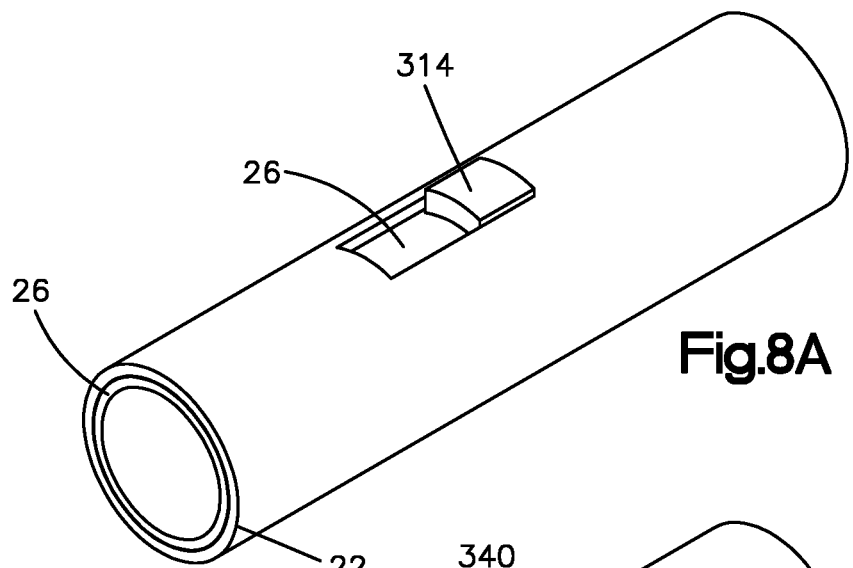
FIG. 8A is a perspective view showing the tensioning element in a first position.
Figure 8B:
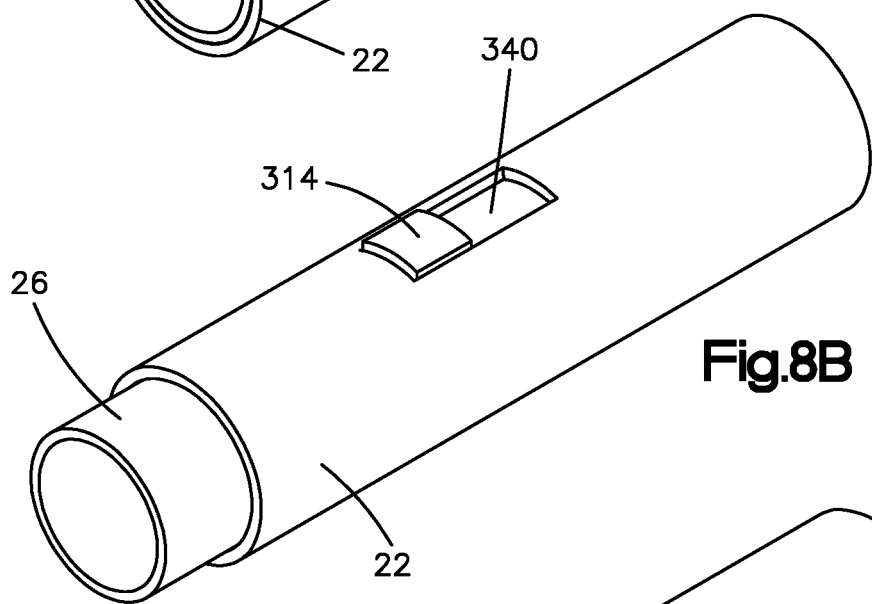
FIG. 8B is a perspective view showing the release component moved proximally and abutting the tensioning element.
Figure 8C:
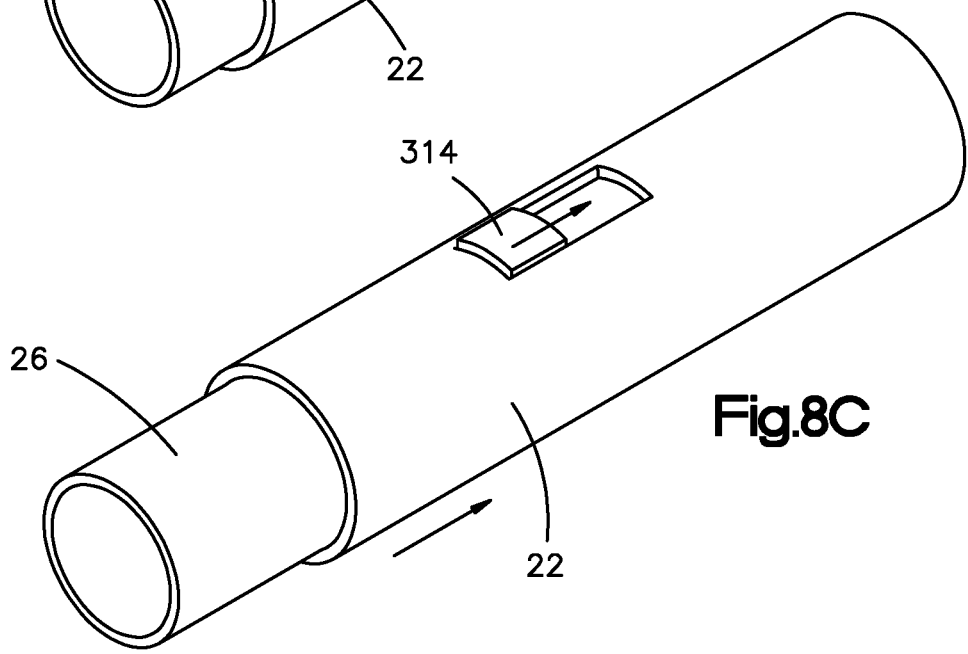
FIG. 8C is a perspective view showing the release component moved further proximally.

FIGS. 8A-9C shows the relative positions of the shuttle 314, the release component 22 and delivery component 26 as the release component 22 is moved proximally. As shown in FIGS. 8A and 9A, the toggle 40 is restrained by the release component (not shown) and shuttle 314 is disposed in the guide portion 334. As shown in FIGS. 8B and 9C, further movement of the release component 22 in the proximal direction 4 release the toggle 40 as discussed above, and advances the distal edge 351 against the shuttle 314. Further, as the shuttle 314 is pulled proximally, the crimp 318 will be received within the channel 322 of the shuttle 314 to thereby fix the shuttle 314 to the suture 44. As shown in FIGS. 8B and 9C, further movement of the release component 22 in the proximal direction 4 advances the distal edge 351 against the shuttle 314 causing the distal edge 351 to push the shuttle 314 from the guide portion 334 into the drop portion 340 as shown in FIGS. 8C and 9C so that the shuttle 314 will drop into the delivery tube channel 84. Because suture 44 is being pulled proximally via the actuator as discussed above, tension is being applied to the suture 44.

The release component and delivery components 22 and 26 are described above as having tubular shaped bodies. It should be appreciated that the release and delivery components can have other configurations. For instance, the release component can be an elongate rod, or an elongate rod with a tubular ring coupled to its distal end. The delivery component can be configured such that only a portion thereof has a tubular shape.

Embodiments of the present technology will now be described with respect to exemplary large bore procedures that utilize the vascular closure device 10. In order to perform any of the related procedures, the user gains percutaneous access to, for example, the femoral artery, causing a puncture site in the artery. To gain percutaneous access to the artery, the Seldinger technique may be used. For example, a hollow bore needle is inserted into the artery. A guide wire 150 is then advanced through the hollow needle and into the femoral artery a sufficient distance to allow removal of the needle without the guide wire 150 pulling out of the vessel. Removing the needle leaves the guide wire 150 in place, with a portion of the guide wire 150 extending into the artery. The guide wire 150, extending from outside the patient into the femoral artery, provides for an entry guide for other medical devices including the vascular closure device 10. Therefore, once the guide wire 150 is positioned in the vessel of the patient, catheters, or introducers, of gradually increasing diameters are advanced over the guidewire and through the puncture into the artery to further open the puncture site. Then, an introducer/procedure access sheath set (i.e. an introducer inside an access tube or sheath) is moved along the guide wire 150 such that a distal end of the sheath moves into the vessel through the puncture site. And once positioned, the introducer can be removed such that the sheath provides for sizable access to the vessel interior from outside the body.

After the relevant procedure is completed, the puncture site in the artery created by the bore needle during percutaneous access of the artery may be closed. The vascular closure device 10 may be used to seal the puncture site. FIGS. 10A-10H show schematic views of the vascular closure device 10 during the process of closing a puncture site 200 in a vessel (e.g. artery) wall 204.

Now in reference to FIG. 10A, to deliver the vascular closure device 10 to the puncture site 200 so that the closure device 10 can seal the puncture site 200, the introducer/procedure sheath set is replaced with a closure access sheath 208. For example, as shown in FIG. 10A, the procedure sheath is exchanged for the closure access sheath 208 by removing the procedure sheath from the patient, leaving the guide wire 150 in place, and subsequently moving the closure access sheath 208 along the guide wire 150 or otherwise positioning the access sheath 208, such that a portion of the access sheath 208 is disposed within the vessel through the puncture site 200. As shown in FIG. 10A, the access sheath 208 defines a distal end $D_A$, a proximal end $P_A$, and an access channel 212 that extends from the proximal end $P_A$ to the distal end DA along an insertion direction I. The access sheath 208 further includes a sheath hub 216 at its proximal end $P_A$. The sheath hub 216 is configured to couple to the vascular closure device 10 when the vascular closure device 10 is inserted into the access channel 212 along the insertion direction I.

Figure 10B:
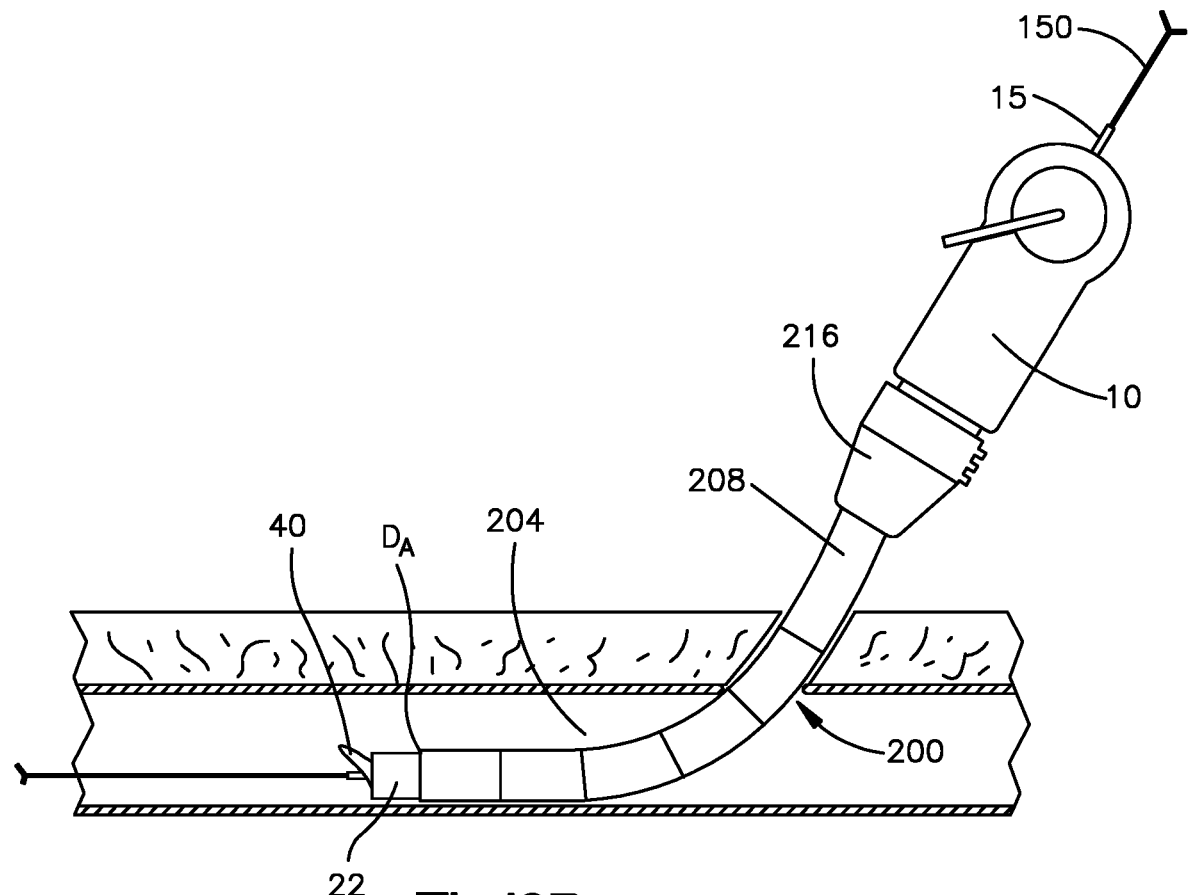
FIG. 10B is a schematic showing the closure device of FIG. 1A translated into an access channel of the access sheath such that a distal end of the toggle is positioned distal to a distal end of the access sheath and over a guidewire.

As shown in FIG. 10B, the vascular closure device 10 can be positioned by translating the vascular closure device 10 into the access channel 212 along the insertion direction I such that the toggle 40 protrudes from the distal end $D_A$ of the access sheath 208 and into the vessel. Once fully inserted, the vascular closure device 10 can couple to the sheath hub 216. As shown in FIG. 10B, a proximal end of the toggle 40 is trapped within the release component 22 between the release component 22 and the delivery component 26 while the vascular closure device 10 is being moved into the vessel through the puncture site 200 of the vessel. While the proximal end of the toggle 40 is trapped, the toggle 40 is oriented in a pre-sealing position whereby at least the proximal end of the toggle 40 is prevented from dragging against the vessel wall during positioning of the toggle 40 within the vessel.

Once the vascular closure device 10 is properly positioned within the access sheath 208, the toggle 40, and in particular, the entire access sheath 208 and vascular closure device 10 combination can be moved proximally such that the toggle 40 is adjacent the puncture site 200. While the toggle 40 is being positioned adjacent the puncture site 200 the toggle 40 is in the pre-sealing position as shown in FIG. 10C. And once the toggle 40 is in position, the actuator 38 is actuated to thereby release the toggle 40 from the release tube and subsequently apply a tension to the suture 44 so as to pull the toggle 40 against the distal end of the delivery component 26 as shown in FIG. 10D. At this point the toggle 40 will be oriented in a sealing position as shown in 10D.

Figure 10G:
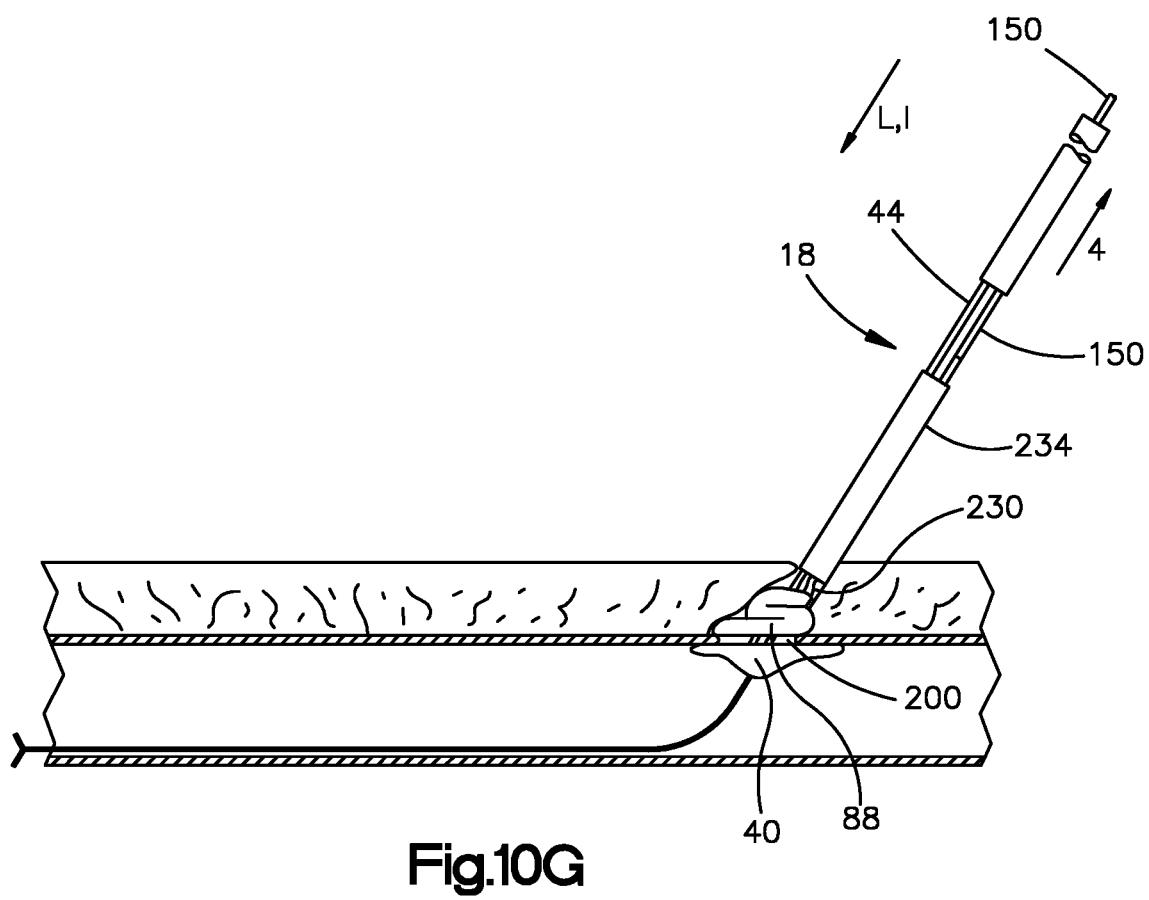
FIG. 10G is a schematic showing deployment of a locking member against the plug.

With the toggle 40 in the sealing position as shown in FIG. 10E, the deployment device 14 along with the access sheath 208 can together be pulled proximally such that the toggle 40 abuts the vessel wall 204. As shown in FIG. 10F, further pulling of the device 14 and sheath 208 will cause the sealing device 18, including the toggle 40, plug 88, a locking member 230, suture 44, and a tamper 234, to be fully withdrawn from the delivery component 26. By pulling on the suture 44 in a direction away from the vessel (i.e. in a direction opposite the insertion direction I) the suture 44 is tensioned and the toggle 40 is moved fully into position against an inner surface of the vessel wall at the puncture site 200. The tension in the suture 44 also pulls the plug 88 into the puncture site 200, and causes the plug 88 to substantially fill the puncture site 200 as shown in FIG. 10G. After the plug 88 is in contact with blood or other fluids within the puncture site 200, the plug 88 will expand and fill the remainder of the puncture site 200.

Figure 10H:
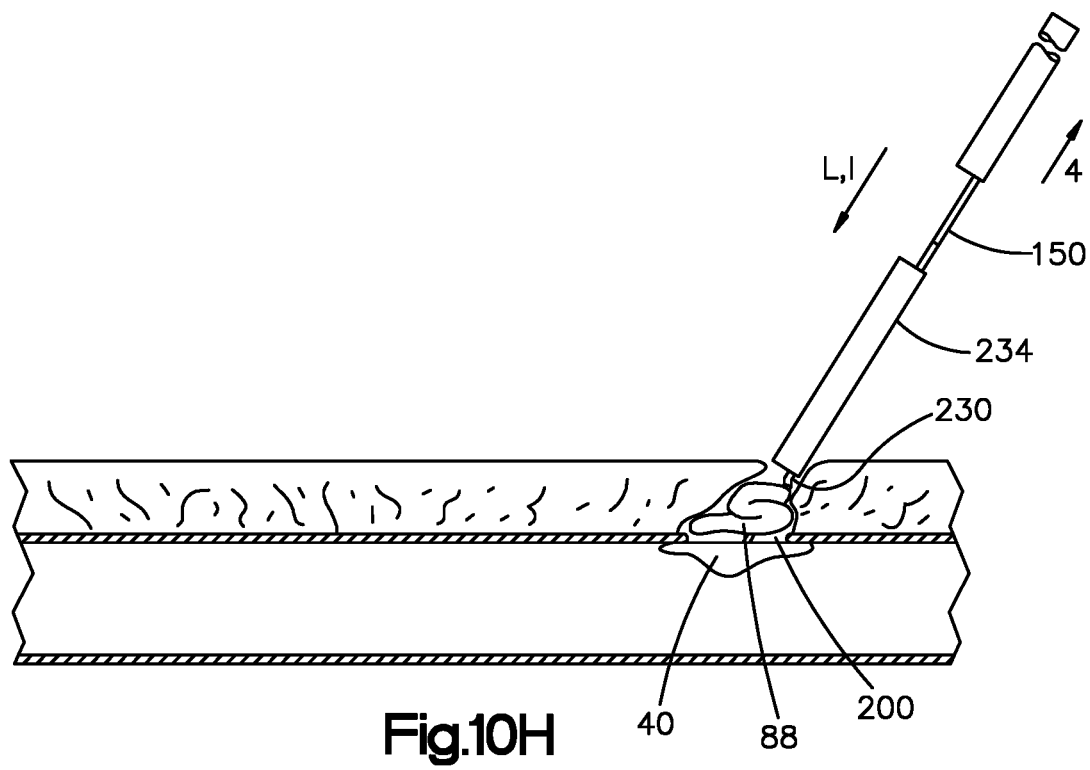
FIG. 10H is a schematic showing the locking member being tamped against the plug with a tamper.

After the user has pulled the suture 44 to cause tension in the suture 44 and to cause the plug 88 to enter the puncture site 200, the user advances the tamper 234 along the guide wire 150 and the suture 44. As shown in FIG. 10H, the tamper 234 contacts the locking member 230 and advances the locking member 230 along the suture 44 until the locking member 230 contacts the plug 88 and presses the plug 88 against an outer surface of the vessel. As the plug 88 is compressed by the tamper 234 the plug 88 folds over the top of and inside the puncture site 200. It should be appreciated, however, that in some embodiments, the delivery component 26 is pulled such that the plug 88 is removed from the delivery component 26 within the release component 22 and the tamper 234 is employed within the release component 22. In such an embodiment, the release component 22 helps control the plug 88 as it is being tamped against the puncture site.

Figure 10I:
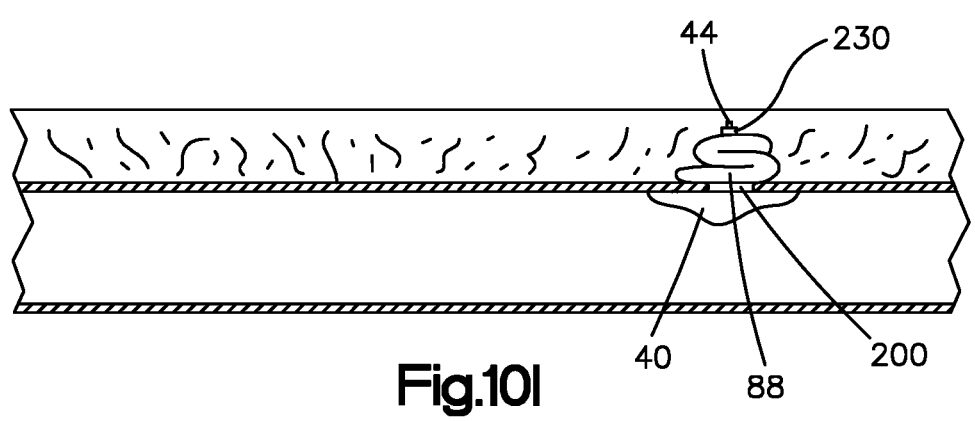
FIG. 10I is a schematic showing the deployment of the sealing device fully sealing the puncture site.

As shown in FIG. 10H, the locking member 230, together with the plug 88 and the toggle 40 effect a seal of the puncture site 200. As shown in FIG. 10H, tension is maintained on the suture 44 throughout the deployment of the plug 88 from the delivery component 26. After the puncture site 200 is sealed, the guide wire 150 can be removed as shown in FIG. 10I. As the guide wire 150 is removed, the suture 44 remains in tension and the user can re-compress the plug 88 with the tamper 234 as desired to confirm a proper seal of the puncture site 200. Once properly sealed, the suture 44 can be cut so that the remaining suture 44, tamper 234, and other components of the sealing device 18 can be removed from the puncture site 200, as shown in FIG. 10I. Remaining portions of the sealing device 18, including the toggle 40, plug 88, portion of suture 44, and locking member 230 (depending on material used) will resorb into the body of the patient over time.

While the foregoing description and drawings represent the preferred embodiment of the present invention, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the present disclosure may be used with many modifications of structure, arrangement, proportions, materials, and components, which are particularly adapted to specific environments and operative requirements without departing from the principles of the present disclosure. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the present disclosure being indicated by the appended claims, and not limited to the foregoing description.

It will be appreciated by those skilled in the art that various modifications and alterations of the present disclosure can be made without departing from the broad scope of the appended claims. Some of these have been discussed above and others will be apparent to those skilled in the art.

We claim:

1. A vascular closure device comprising:
   a delivery device that is elongate along a longitudinal direction, the delivery device having a distal end and a proximal end spaced from the distal end along the longitudinal direction a release component that is elongate along the longitudinal direction, and a delivery component that extends along the release component along the longitudinal direction;
   an anchor that is at least partially captured by the delivery device;
   a suture attached to the anchor and that extends along the delivery device in a proximal direction toward the proximal end of the delivery device;
   a tensioner having a drag member through which the suture extends; and
   at least one actuator that is coupled to the suture and the delivery device,
   wherein the at least one actuator is configured to move one or more components of the delivery device to release the anchor from the delivery device and apply a tensional force to the suture;
   wherein the release component defines a first engagement member and the at least one actuator includes a second engagement member that is engaged with the first engagement member such that rotation of the at least one actuator causes the release component to translate along the longitudinal direction.

2. The vascular closure device of claim 1, wherein when the at least one actuator has been actuated, the tensional force applied to the suture urges the anchor against the distal end of the delivery device.

3. The vascular closure device of claim 1, wherein further comprising a plug that is attached to the suture relative to the anchor in the proximal direction.

4. The vascular closure device of claim 1, further comprising a tamper that extends along the suture and is positioned proximal relative to the anchor.

5. The vascular closure device of claim 1, further comprising a guide lumen that extends through the delivery device, wherein the guide lumen is sized and configured to receive a guidewire therethrough.

6. A vascular closure device comprising:
a release component that is elongate along a longitudinal direction;
a delivery component that extends along the release component along the longitudinal direction;
an anchor that is at least partially disposed within the release component;
a suture attached to the anchor and that extends along the delivery component in a proximal direction toward a proximal end of the release component; and
at least one actuator that is coupled to the suture and at least one of the release component and the delivery component, such that, actuation of the at least one actuator causes (i) at least one of the release component and the delivery component to move relative to the other of the release component and the delivery component so as to release the anchor from the release component, and (ii) the suture to be pulled in the proximal direction to thereby place the suture in tension and urge the anchor against a distal end of the delivery component such that the anchor is oriented in a sealing position.

7. The vascular closure device of claim 6, further comprising a tensioner having a drag member that is configured to apply a frictional force that maintain the suture in tension after the at least one actuator has been actuated and the anchor has been urged against the distal end of the delivery component.

8. The vascular closure device of claim 7, wherein the frictional force applied to the suture by the drag member is high enough to maintain the suture in tension after the at least one actuator has been actuated and the anchor has been urged against the distal end of the delivery component.

9. The vascular closure device of claim 7, wherein the release component defines a guide track, wherein the suture extends around the guide track into the tensioner such that as the release component is pulled in the proximal direction, the guide track pulls the suture in the proximal direction.

10. The vascular closure device of claim 6, wherein the release component defines a first engagement member and the at least one actuator includes a second engagement member that is engaged with the first engagement member such that rotation of the at least one actuator causes the release component to translate along the longitudinal direction.

11. The vascular closure device of claim 6, wherein further comprising a plug that is attached to the suture relative to the anchor in a proximal direction, wherein the proximal direction extends from a distal end of the release component toward the proximal end of the release component.

12. A vascular closure device comprising:
at least one actuator;
a release component having a distal end, a proximal end, and a release component channel that extends from the distal end toward the proximal end along a longitudinal direction;
a delivery component having a distal end and a proximal end, wherein at least one of the release component and the delivery component is movable relative to the other upon actuation of the at least one actuator;
a tensioner that contains a drag member; and
an anchor that is at least partially disposed within the release component; and
a suture attached to the anchor, the suture extending into the tensioner and through the drag member such that the drag member applies a frictional force against the suture;
wherein actuation of the at least one actuator moves at least one of the delivery component and the release component relative to the other to 1) release the anchor from the release component and 2) apply a tensional force to the suture to urge the anchor against the distal end of the delivery component such that the anchor is oriented in a sealing position.

13. The vascular closure device of claim 12, further comprising a plug that is attached to the suture relative to the anchor in a proximal direction that extends from the distal end of the release component toward the proximal end of the release component.

14. The vascular closure device of claim 12, wherein the at least one actuator is coupled to the release component and the suture such that actuation of the at least one actuator causes (i) the release component to move in a proximal direction relative to the delivery component to release the anchor from the release component, and (ii) the suture to be pulled in the proximal direction to thereby urge the anchor against the distal end of the delivery component such that the anchor is oriented in the sealing position.

15. The vascular closure device of claim 12, wherein the at least one actuator is a lever.

16. The vascular closure device of claim 12, further comprising a tamper that extend along the suture and is positioned proximal relative to the anchor.

17. The vascular closure device of claim 12, further comprising a guide lumen, wherein the guide lumen is sized and configured to receive a guidewire therethrough.

18. The vascular closure device of claim 12, further comprising a plug that is attached to the suture relative to the anchor in a proximal direction, wherein the proximal direction extends from the distal end of the release component toward the proximal end of the release component.

* * * * *